United States Patent
Becker et al.

(10) Patent No.: US 9,353,244 B2
(45) Date of Patent: May 31, 2016

(54) MIXTURE OF SUCCINIC ESTERS AS PLASTICIZER

(75) Inventors: Hinnerk Gordon Becker, Essen (DE); Michael Graβ, Haltern am See (DE)

(73) Assignee: Evonik Degussa GmbH, Essen (DE)

( * ) Notice: Subject to any disclaimer, the term of this patent is extended or adjusted under 35 U.S.C. 154(b) by 281 days.

(21) Appl. No.: 14/008,425

(22) PCT Filed: Feb. 27, 2012

(86) PCT No.: PCT/EP2012/053285
§ 371 (c)(1),
(2), (4) Date: Nov. 22, 2013

(87) PCT Pub. No.: WO2012/130545
PCT Pub. Date: Oct. 4, 2012

(65) Prior Publication Data
US 2014/0069299 A1    Mar. 13, 2014

(30) Foreign Application Priority Data
Mar. 31, 2011   (DE) .......................... 10 2011 006 557

(51) Int. Cl.
| | |
|---|---|
| *C08K 5/11* | (2006.01) |
| *C08K 5/10* | (2006.01) |
| *C07C 69/40* | (2006.01) |
| *C09J 11/06* | (2006.01) |
| *C10M 105/36* | (2006.01) |
| *C10M 129/72* | (2006.01) |

(52) U.S. Cl.
CPC . *C08K 5/11* (2013.01); *C07C 69/40* (2013.01); *C09J 11/06* (2013.01); *C10M 105/36* (2013.01); *C10M 129/72* (2013.01); *C08K 5/10* (2013.01)

(58) Field of Classification Search
CPC ............ C07C 69/40; C08K 5/11; C08K 5/10; C09J 11/06; C10M 105/36; C10M 129/72
See application file for complete search history.

(56) References Cited

U.S. PATENT DOCUMENTS

| | | | | |
|---|---|---|---|---|
| 5,104,492 | A * | 4/1992 | King | ....................... C07C 51/48 203/15 |
| 6,212,755 | B1 * | 4/2001 | Shimada | ................ B29C 45/14 264/272.15 |
| 8,022,244 | B2 | 9/2011 | Grass et al. | |
| 8,258,325 | B2 | 9/2012 | Grass et al. | |
| 2003/0092808 | A1 * | 5/2003 | Stanhope | ............... C08K 5/103 524/291 |
| 2005/0038285 | A1 | 2/2005 | Maschmeyer et al. | |
| 2007/0060768 | A1 | 3/2007 | Grass et al. | |
| 2010/0261628 | A1 | 10/2010 | Scherer et al. | |
| 2011/0046283 | A1 | 2/2011 | Grass et al. | |
| 2012/0202725 | A1 | 8/2012 | Grass et al. | |
| 2012/0220507 | A1 | 8/2012 | Grass et al. | |

FOREIGN PATENT DOCUMENTS

| | | |
|---|---|---|
| DE | 10 2006 001 768 A | 7/2007 |
| DE | 10 2008 002 166 A1 | 12/2009 |
| JP | H09263731 * | 10/1997 |
| WO | WO 03/029181 A1 | 4/2003 |

OTHER PUBLICATIONS

English Translation of JPH09263737, p. 1-46, Oct. 1997.*
Kocz et al., "A Convenient Triphosgene-Mediated Synthesis of Symmetric Carboxylic Acid Anhydrides," J. Org. Chem., 59, 2913-2914.*
U.S. Appl. No. 14/001,177, filed Aug. 23, 2013, Becker, et al.
U.S. Appl. No. 14/001,597, filed Oct. 8, 2013, Becker, et al.
International Search Report issued Aug. 10, 2012, in PCT/EP2012/053285, filed Feb. 27, 2012 (with English-language translation).
Saechtling: "Kunststoff Taschenbuch", HANSER, XP 002678379, 2001, pp. 452-455.

* cited by examiner

*Primary Examiner* — Paul A Zucker
*Assistant Examiner* — Mark Luderer
(74) *Attorney, Agent, or Firm* — Oblon, McClelland, Maier & Neustadt, L.L.P.

(57) ABSTRACT

Mixture of succinic esters, which is characterized in that the alkyl radical has a proportion of alkyl components having less than 9 carbon atoms of not more than 15% by mass, the alkyl radical has a proportion of alkyl components having more than 9 carbon atoms of not more than 25% by mass and the proportion of 3,5,5-trimethylhexyl radicals is not more than 5 mol % and the proportion of linear n-nonyl radicals is not more than 15 mol %.

21 Claims, No Drawings

MIXTURE OF SUCCINIC ESTERS AS PLASTICIZER

The present invention relates to mixtures of succinic esters, methods of producing these mixtures, compositions containing said mixtures, and the use of succinic ester mixtures as such or in compositions.

Polyvinyl chloride (PVC) is among the economically most important polymers. It finds various applications both as rigid PVC and as flexible PVC.

To produce flexible PVC, plasticizers are added to PVC, and phthalate esters, especially di-2-ethylhexyl phthalate (DEHP), diisononyl phthalate (DINP) and diisodecyl phthalate (DIDP), are employed in the vast majority of cases. Owing to existing and possibly future legally-enforceable regulations on the use of phthalates, there is a need to find new esters suitable as plasticizers for PVC. Furthermore, PVC plasticizers are at present mainly formed from raw materials that are mainly derived from petroleum refining. Since petroleum reserves are finite, sustainable use of alternative sources is required. In this connection, in particular hydroxy compounds (for example alcohols) and/or carboxylic acids are possible raw materials for plasticizers. In this case, however, there are problems of poor availability, variable quality and low purity of most of the "renewable" compounds that may come into consideration, so that there is a limited choice of "bio-raw materials" usable on a large scale currently or in the medium term.

Succinic acid can be produced both petrochemically (e.g. by hydrogenation of maleic acid) and biotechnologically, and in the latter case renewable raw materials can be used particularly advantageously to obtain succinic acid. Succinic acid is of widespread natural occurrence, e.g. as a metabolic product in the citric acid cycle, in many fruits and vegetables, wood, fungi, lichen etc.; succinic acid is in addition also a by-product of alcoholic fermentation. Various anaerobic microorganisms form succinic acid as a fermentation product from sugars and cellulose. The rumen bacterium *Actinobacillus* and the nonrumen bacterium *Anaerobiospirillum* are of industrial importance; these produce succinic acid at a yield of 83-87% from glucose or corn-steep liquor in batch cultures [Römpp Chemielexicon; online edition; access 06/2009].

U.S. Pat. No. 6,355,711 (ExxonMobil; 1998) describes the production of plasticizers based on branched oxo alcohols. In addition to phthalates, adipates and trimellitates, a great many other carboxylates are also mentioned, including esters of succinic acid. However, the alcohol components described have methyl branching on the β-carbon atom to at least 50%, with 3-methyloctanol, 7-methyloctanol and 2,6-dimethylheptanol stated as the main components. However, the high proportion of branchings on the β-carbon atom is a disadvantage both for esterification and for plasticizer action.

DE10043545 (Evonik Oxeno; 2000) describes a method of producing carboxylate esters, which in addition to other fields of application, in particular can also be used as plasticizers for plastics. It also mentions, among others, succinic acid as aliphatic carboxylic acid and isononanol as aliphatic alcohol. DE10043545 does not, however, contain any teaching on the specific composition of the nonanols and on the specific material properties of the esters or of the PVC blends that can be produced with them. Furthermore, it does not relate to esters that are produced on the basis of renewable raw materials.

The same applies to the mixtures of esters of polyfunctional carboxylic acids that are produced on the basis of aliphatic branched monofunctional alcohols, which are described in U.S. Pat. No. 2,015,077 and U.S. Pat. No. 2,015,088 (DuPont; 1932). Admittedly succinic acid is also stated, among others, as an example of polyfunctional carboxylic acid, and 4,6-dimethyl-1-heptanol, 4,6-dimethyl-1-octanol and 3-methyl-3-octanol, among others, are mentioned as examples of monofuctional aliphatic branched alcohols. However, on the one hand the aforementioned alcohols are not available in sufficient quantities on an industrial scale as pure substances, and on the other hand in the case of 3-methyl-3-octanol, a secondary alcohol, deleterious effects in industrial application must also be assumed owing to the branching present directly on the ester group. Furthermore, it too does not relate to esters that are obtainable on the basis of renewable raw materials.

Regarding the use of renewable raw materials in the production of plasticizers, EP 1005562 (Michigan State University; 1998) discloses a process for preparing and purifying succinic acid, which is produced from carbohydrates by fermentation. However, there is no direct link to particular succinate esters or use thereof as PVC plasticizer.

EP 1849764 and US2006/0252956 (Michigan State University; 2006) relate to a process for producing carboxylate esters via reactive distillation, wherein the acid component is preferably produced on the basis of renewable raw materials ("biomass-based"). However, in this case in particular linear and/or "lower alcohols" with 1 to 8 carbon atoms are used for the esterification, focusing especially on ethanol and especially on ethyl citrate. There is little description of the use of nonyl alcohols, or of the advantages and/or disadvantages of particular succinate esters when used as PVC plasticizers. Linear short-chain esters are volatile, and longer-chain esters tend to undergo crystallization, which has an adverse effect on the material properties especially in compositions and the products produced from them.

Accordingly, the succinate esters currently known have technical, economic, toxicological and ecological disadvantages. Technically, in particular the volatility of short-chain aliphatic succinate esters is too high, and so is their migration rate. In addition, in the case of the longer-chain succinate esters (especially those with a linear alcohol component), in addition to inadequate gelling, they have poor compatibility with polymers (especially polyvinyl chloride) and formulation additives (for example antifoaming agents, stabilizers, viscosity additives etc.), which leads to clouding in the end product and to exudation, and makes reasonable commercial application impossible. A particular economic disadvantage is the difficult access to alcohol components (pure substances) of many known succinate esters. Toxicologically, in particular the use of succinate esters that have quaternary carbon atoms is problematic, as these are difficultly biodegradable and therefore have a tendency toward bioaccumulation. Ecologically, however, succinate esters that are based only on fossil petrochemical constituents are to be assessed as nonsustainable and offering little safeguarding of the future.

Therefore, for the aforementioned reasons, the succinate esters mentioned hitherto in the prior art are not, or not sufficiently, suitable to allow significant application in industrially relevant recipes.

Based on the known prior art, the problem was therefore to provide succinate esters that can be used as plasticizers for plastics such as PVC, PVB or PAMA and with which the aforementioned technical, economic, toxicological and ecological problems do not occur or only occur to a much diminished extent.

The problem is solved with a mixture of succinate esters, characterized in that the alkyl residue has a proportion of alkyl components with less than 9 carbon atoms of max. 15 wt %, the alkyl residue has a proportion of alkyl components with more than 9 carbon atoms of max. 25 wt %, and in that the proportion of 3,5,5-trimethylhexyl residues is max. 5 mol % and the proportion of linear n-nonyl residues is max. 15 mol %.

It was found, surprisingly, that special mixtures of isomeric nonyl esters of succinic acid can be used as plasticizers for plastics, especially PVC, and in this application display advantageous properties relative to the succinate esters already known from the literature, wherein with respect to the alcohol component, in particular only a small proportion of more highly branched alcohols (for example 3,5,5-trimethyl-1-hexanol) with simultaneous presence of only limited proportions of linear nonyl alcohol is decisive for industrial usability.

In one embodiment of the invention, the proportion of succinic acid relative to all parts of succinic acid that are present in the mixture as ester based on renewable raw materials is at least 10 mol %.

The acid component that is used for preparing the mixtures of esters according to the invention is succinic acid, and the proportion of succinic acid based on renewable raw materials in the production process according to the invention and therefore also in the ester mixture according to the invention can be up to 100 mol %.

Succinic acid can be produced both petrochemically (e.g. by hydrogenation of maleic acid) and biotechnologically, and in the latter case renewable raw materials can be used especially advantageously for producing succinic acid.

Preferably the proportion of succinic acid that was obtained using renewable raw materials is at least 10 mol %, especially preferably at least 30 mol %, especially preferably at least 50 mol % and quite especially preferably at least 70 mol % of the succinic acid used for preparing the mixtures of esters according to the invention.

Regarding the raw material basis of this embodiment, the special feature of the present invention is the use of renewable raw materials for preparing the succinic acid mixtures. In the sense of the present invention, renewable raw materials, in contrast to petrochemical raw materials, which are based on fossil resources, for example petroleum or coal, are those raw materials that are formed or are produced on the basis of biomass. The terms "biomass", "bio-based" or "based on" or "produced from renewable raw materials" comprise all materials of biological origin, which originate from the so-called "short-term carbon cycle", and therefore are not a constituent of geological formations or fossil deposits. In particular, "based on renewable raw materials" and "on the basis of renewable raw materials" mean that, using ASTM method D6866-08 ($^{14}$C method), the corresponding proportion of $^{14}$C isotopes can be detected in the mixture of succinic acid or in the mixture of succinate esters.

The identification and quantification of renewable raw materials can be carried out according to ASTM method D6866. A characteristic feature of renewable raw materials is, among other things, their proportion of the $^{14}$C carbon isotope, compared to petrochemical raw materials. Using the radiocarbon method, it is possible to determine the proportion of $^{14}$C isotopes and therefore also the proportion of molecules based on renewable raw materials.

A succinic acid nonyl ester has a total of 22 carbon atoms, 2 times 9 from the alkyl residues and 4 from the succinic acid. With a proportion of bio-based succinic acid of 100 mol % it therefore follows that the proportion relative to all carbon atoms in the ester is 4/22=0.1819. This factor varies with the corresponding carbon number of the alkyl residues and therefore with the alcohol mixtures used for esterification. To determine the composition of the alcohol mixture, it can be analyzed by the usual methods of analysis (e.g. by gas chromatography and then mass spectroscopy/"GC-MS"). It is also possible to determine the number of carbon atoms in the alkyl residues of the succinic acid even after esterification (e.g. in which the ester is first saponified completely and then the alcohols released are analyzed). From the maximum possible proportion of bio-based succinic acid, it is then possible to calculate the actual proportion of bio-based succinic acid in the ester mixture.

A particular economic and at the same time ecological advantage of this embodiment is the simultaneous use of renewable raw materials, as source for the acid component, and petrochemical raw materials, as source for the alcohol mixture, for production of the succinate esters according to the invention, which on the one hand makes particularly low-cost production and wide usability possible, but on the other hand also leads to particularly "sustainable" products.

In another embodiment, the proportion of succinate esters that contain at least one 3,5,5-trimethylhexyl residue is max. 5 mol %.

In another embodiment, the mixture contains a proportion of alkyl residues with 9 carbon atoms that have a methyl branching on the second carbon atom after the oxygen of the carboxyl group of max. 49.5 mol %.

In another embodiment the boiling point of the mixture is above 180° C.

In another embodiment the intrinsic viscosity of the mixture determined by shear rheometry with a shear rate of 1/s at a temperature of 20° C. is max. 40 mPa·s.

Moreover, a mixture of succinate esters is claimed, which is characterized in that the alcohol mixture used for preparation has a proportion of alcohol components with less than 9 carbon atoms of max. 15 wt %, a proportion of alcohol components with more than 9 carbon atoms of max. 25 wt %, and the content of 3,5,5-trimethylhexanol in the alcohol mixture is max. 5 mol % and the content of linear n-nonanol in the alcohol mixture is max. 15 mol %.

In one embodiment the proportion of succinic acid or succinic acid derivatives used for production of the esters and based on renewable raw materials is at least 10 mol %.

In one embodiment the proportion of succinate esters that contain at least one 3,5,5-trimethylhexyl residue is max. 5 mol %.

In one embodiment the alcohol mixture used contains a proportion of isomeric alcohols with 9 carbon atoms that have a methyl branching on the β-carbon atom of the alcohol of max. 49.5 mol %.

In one embodiment the alcohol mixture used contains a proportion of isomeric alcohols with 9 carbon atoms that have two methyl branchings of max. 49.5 mol %.

The present invention further relates to ester mixtures produced from isomeric nonyl alcohols and succinic acid, characterized in that the alcohol mixture used for production of the esters has a proportion of alcohol components with less than 9 carbon atoms of max. 15 wt %, and a proportion of alcohol components with more than 9 carbon atoms of max. 25 wt %, and simultaneously the content of 3,5,5-trimethyl-1-hexanol is max. 5 mol % and the content of linear n-nonanol is max. 15 mol %, and the succinic acid used for esterification was produced on the basis of renewable raw materials, or was itself obtained from renewable raw materials.

The present invention further relates to compositions containing the mixtures according to the invention.

In one embodiment the proportion of succinate esters based on isomeric nonyl alcohols is at least 60 wt %, preferably at least 70 wt %, especially preferably at least 80 wt %.

In another embodiment the proportion of succinate esters based on isomeric nonyl alcohols is max. 70 wt %, preferably between 1 and 65 wt %, especially preferably between 2 and 55 wt % and quite especially preferably between 5 and 50 wt %.

The present invention also relates to PVC compositions, especially PVC plastisols, characterized in that in addition to at least one PVC homo- or copolymer they contain 5 to 250 parts by weight of the ester mixture according to the invention per 100 parts by weight PVC.

The present invention also relates to products, intermediates or finished products, floor coverings, wall coverings, awnings, films, profiles, hoses, resists, adhesives, sealants, insulation and sheathing containing the succinate esters according to the invention.

The succinate esters according to the invention have an acid component, i.e. succinic acid, which is preferably obtained from renewable raw materials. Renewable raw materials in the sense of the present invention can be all organic raw materials, which originate for example from agriculture and forestry. Especially preferably they are carbohydrates, especially sugars. The succinic acid is preferably produced in a fermentation process, as is known for example from EP 1005562. This has the advantage that the biochemical processes used for production are particularly energy-efficient.

Especially preferably the succinate esters according to the invention consist of an acid component (succinic acid) produced (e.g. biotechnologically) on the basis of renewable raw materials and two alcohol components (e.g. isomeric nonyl alcohols) produced on a petrochemical basis. This has the advantage that in this way succinate esters are made available that combine sustainability and cost efficiency in production to a quite particular extent.

The alcohol component is preferably obtained by the oxo process, as is known for example from U.S. Pat. No. 2,327,066.

The composition of the alcohol mixtures used for preparing the succinate esters according to the invention can be varied and set within defined limits (e.g. in the context of the oxo process) through the choice of the catalyst or catalysts, the reaction conditions, e.g. in oligomerization, the raw materials used, process control, e.g. with recycling of partial streams, and by appropriate operations of distillation and/or extraction performed on the alcohol product stream.

The alcohol mixtures used for preparing the succinate esters according to the invention have in particular a proportion of alcohol components with less than 9 carbon atoms of max. 15 wt %, preferably of max. 14 wt %, especially preferably of max. 13 wt %, and especially preferably from 0 to 12 wt %, and further lower limits are between 0 and 7 wt %, between 5 and 9 wt % and between 7 and 11 wt %. This has the advantage that the proportion of more highly volatile components is minimized, and therefore the overall volatility of the succinate esters according to the invention is lowered.

Furthermore, the alcohol mixtures used for preparing the succinate esters according to the invention have a proportion of alcohol components with more than 9 carbon atoms of max. 25 wt %, preferably of max. 23 wt %, especially preferably of max. 21 wt % and quite especially preferably from 0 to 20 wt %, and further lower limits are between 0 and 12 wt %, between 6 and 15 wt % and between 9 and 20 wt %. This has the advantage that the proportion of higher-molecular components is minimized and the intrinsic viscosity of the succinate esters according to the invention is low.

Furthermore, the alcohol mixtures used for preparing the succinate esters according to the invention in particular have a proportion of linear n-nonanol of max. 15 mol %, preferably of max. 14 mol %, especially preferably of max. 13 mol %, and quite especially preferably from 0 to 13 mol %, wherein further subgroups are between 2 and 12 mol %, between 3 and 11 mol %, between 2 and 5 mol % and between 4 and 10 mol %. This has the advantage that the proportion of linear succinate esters that have a very limited compatibility with PVC and formulation additives and a higher volatility within the succinate esters according to the invention is minimized.

Furthermore, the alcohol mixtures used for preparing the succinate esters according to the invention in particular have a proportion of isomeric alcohols with 9 carbon atoms with methyl branching on the β-carbon atom of the alcohol of max. 49.5 mol %, preferably of max. 48 mol %, especially preferably of max. 47 mol %, and quite especially preferably from 0 to 45 mol %, wherein further subgroups are between 0 and 18 mol %, between 10 and 44 mol %, between 12 and 42 mol %, between 14 and 41 mol %, between 15 and 35 mol % and between 32 and 42 mol %. This has the advantage that the proportion of alcohols that only esterify slowly on account of steric hindrance is small.

Furthermore, the alcohol mixtures used for preparing the succinate esters according to the invention in particular have a proportion of isomeric alcohols with 9 carbon atoms with two methyl branchings of max. 49.5 mol %, preferably max. 48 mol %, especially preferably max. 47 mol % and quite especially preferably between 0 and 45 mol %, wherein further subgroups are between 5 and 44 mol %, between 12 and 25 mol %, between 14 and 34 mol % and between 36 and 44 mol %. This has the advantage that the proportion of alcohols that lead to succinate esters with high intrinsic viscosity is minimized.

Furthermore, the mixtures of isomeric nonyl alcohols with the empirical formula $C_8H_{17}CH_2OH$ used for preparing the succinate esters according to the invention contain in particular less than 10 mol %, preferably less than 5 mol %, more preferably less than 1 mol % and especially from 0 to 0.5 mol %, preferably less than 0.1 mol %, especially from 0.0001 to 0.1 mol % and especially preferably less than 0.05 mol %, especially from 0.01 to 0.05 mol % of 3,5,5-trimethylhexanol or other triply substituted nonyl alcohols with the empirical formula $C_8H_{17}CH_2OH$, especially those with quaternary carbon atoms. This has the advantage that the proportion of alcohols that lead to succinate esters with high intrinsic viscosity is minimized.

The distributions of isomers of the isomeric nonyl alcohols in the mixtures can be determined with the usual methods of measurement familiar to a person skilled in the art, such as NMR spectroscopy, GC or GC/MS spectroscopy, preferably after conversion to the silyl or methyl esters, optionally after prior purification or separation by methods of liquid chromatography (e.g. HPLC).

Very good fluidity and low intrinsic viscosity can be achieved when in particular the proportion of multiply branched molecules, especially of trimethyl-1-hexanol, is kept as low as possible. The succinate esters according to the invention therefore contain only very small amounts of esters that contain, as alcohol components, trimethyl-1-hexanol, for example 3,5,5-trimethylhexanol, or other alcohol components with quaternary carbon atoms. In particular, in the ester mixture according to the invention the proportion of succinate ester that contains at least one 3,5,5-trimethylhexyl residue is max. 10 wt %, preferably max. 8 wt %, especially preferably max. 6 wt % and quite especially preferably max. 5 wt %.

The succinate esters according to the invention consist of an acid component (succinic acid) and an alcohol component (mixture of isomeric nonyl alcohols). In order to obtain a succinate ester with an intrinsic viscosity as low as possible, the mixture of isomeric nonyl alcohols used for producing the succinate esters has in particular a maximum shear viscosity (at 20° C.) of 20 mPa*s, preferably of max. 15 mPa*s and especially preferably of max. 12 mPa*s.

The mixtures of diisononyl succinates according to the invention or the diisononyl succinates themselves can be produced in all ways known in the prior art, and preferably by the method described below.

In addition to the mixture itself, a method of production thereof is also claimed.

Said method of producing the mixtures described above comprises contacting succinic acid or dimethyl succinate with a mixture of isomeric C9 alcohols, with liberation of water or methanol; using up to 50% stoichiometric excess of the mixture of isomeric C9 alcohols, and carrying out the reaction using a catalyst, selected in particular from the group comprising butyl titanate, nonyl titanate.

In one variant of the process the proportion of succinic acid or succinic acid derivatives used for production of the esters and based on renewable raw materials is at least 10 mol %.

In one variant of the process, succinic acid is esterified with a mixture of isomeric nonanols, called isononanols hereinafter, optionally in the presence of a catalyst with liberation of water.

In another variant of the process dimethyl succinate is transesterified with a mixture of isomeric nonanols with liberation of methanol, optionally using a catalyst, to a mixture of isomeric nonyl esters of succinic acid.

A particular embodiment of the process according to the invention is characterized in that the proportion of succinic acid diesters of n-nonanol in the ester mixture obtained is max. 20 wt % and the proportion of succinic acid diesters of 3,5,5-trimethylhexanol in the ester mixture obtained is max. 10 wt %.

The process according to the invention for producing isomeric nonyl esters of succinic acid is characterized, in a variant of the process, in particular in that succinic acid or a dialkyl succinate ester, especially dimethyl succinate, is reacted with a mixture of isomeric nonanols, using a catalyst. Especially preferably, in the reaction of succinic acid or succinic acid derivatives, a 50% stoichiometric excess of isononyl alcohol(s) is used. Brønsted and/or Lewis acids for example can be used as catalysts, and the use of sulfuric acid, methylsulfonic acid, titanates and oxalates is especially preferred. In a particular preferred embodiment either butyl titanate or nonyl titanate is used as esterification catalyst, wherein the use of nonyl titanate is especially preferred, and has the advantage that fewer by-products can form by transesterification. The reaction temperature during the esterification is between 150 and 250° C., and during esterification there is continuous separation of low-molecular reaction products, for example water. The esterification takes place either continuously or discontinuously, e.g. in batch mode, and especially preferably the esterification takes place discontinuously. In principle, all reactor types known in the prior art can be used as the reaction vessel (after appropriate adaptation), and the use of a stirred vessel is especially preferred, particularly for a reaction carried out discontinuously. In the case of a continuous reaction, preferably cascades of stirred vessels and/or tubular reactors are used, and when using the latter, the low-molecular reaction products must be removed in one or more separate process steps (e.g. by combining the tubular reactor with a stirred vessel with distillation column or by using evaporators). In an especially preferred embodiment, for quantitative distillation of the low-molecular component(s), an auxiliary substance is added, with addition of nitrogen gas being especially preferred. The progress of the reaction is monitored by determining the acid number (according to DIN EN ISO 2114) and by gas chromatography, wherein an acid number of <0.1 mg KOH/g is taken as a measure for attainment of complete conversion of succinic acid. The reaction time (from the time when the reaction mixture begins to boil) is in particular between 60 and 500 minutes, preferably between 70 and 400 minutes, especially preferably between 80 and 300 minutes, and quite especially preferably between 90 and 250 minutes. Following esterification, working-up of the reaction mixture takes place, comprising decomposition and/or separation of the esterification catalyst used and purification of the reaction mixture (e.g. by distillation).

Furthermore, succinyl dichloride, which is obtainable by reaction of succinic acid with chlorinating agents, for example thionyl chloride, can be used as starting substance for preparing the diisononyl esters.

In a particular preferred embodiment, succinic acid and/or methyl succinate and a mixture of isomeric nonyl alcohols—which are obtained from an oxo process—are used as starting substances for preparing the succinate esters according to the invention. Isomeric nonyl alcohols that are produced by an oxo process based on butenes, e.g. based on so-called cracked $C_4$ refinery cuts, are especially preferred.

Preferably a mixture of isomeric nonanols is used, which has at least two nonanols with the empirical formula $C_8H_{17}CH_2OH$ with different constitutional formula, wherein none of the nonyl alcohols present in the mixture has a proportion of more than 50 mol %, preferably at least 49.5 mol %.

The mixtures according to the invention have a low volatility, which minimizes plasticizer losses through evaporation in the end use and/or during the production process. The boiling point of a mixture of isomers is also determined by its composition and to that extent is a characteristic feature. The boiling point at atmospheric pressure of the succinate esters according to the invention, determined by differential scanning calorimetry (tangential method), is in particular above 180° C., preferably above 190° C., especially preferably above 200° C. and quite especially preferably above 210° C.

The mixtures according to the invention have a low intrinsic viscosity, which is particularly advantageous for the production of flexible PVC pastes, as this also leads to a low paste viscosity and therefore to particularly good fluidity of the pastes and particularly good processing properties. The intrinsic viscosity of the succinate esters according to the invention is well below that of the phthalates producible with the same alcohol component. In particular, the intrinsic viscosity of the succinate esters according to the invention determined by shear rheometry at a shear rate of 1/s and at a temperature of 20° C. is max. 40 mPa*s, preferably max. 35 mPa*s, especially preferably max. 30 mPa*s and quite especially preferably max. 25 mPa*s. In particular, the intrinsic viscosity determined by shear rheometry (20° C.; shear rate: 1/s) is between 5 and 30 mPa*s, especially preferably between 7 and 28 mPa*s and quite especially preferably between 9 and 25 mPa*s. This is especially advantageous to the extent that there is a clear viscosity difference for example relative to the current standard plasticizer diisononyl phthalate (intrinsic viscosity >70 mPa*s), which when used in formulations (e.g. in PVC pastes) leads to greatly reduced paste viscosities, and therefore makes faster machine speeds possible (e.g. in spread coating).

Especially preferably, the mixtures according to the invention are colorless and transparent, and are therefore suitable in particular (but not exclusively) for use in (pigmented or unpigmented) white and/or transparent PVC applications (e.g. top coat, calender films etc.). In particular, the succinate esters according to the invention have a color number determined photometrically according to the Hazen/APHA color number scale of max. 50, preferably of max. 45, especially preferably of max. 40 and quite especially preferably of max. 30. In a particular embodiment the color number determined photometrically according to the Hazen/APHA color number scale is between 1 and 30, preferably between 2 and 25, especially preferably between 3 and 20 and quite especially preferably between 4 and 15. This has the advantage that the succinate esters according to the invention with very low Hazen/APHA color numbers (i.e. <20) are suitable in particular for use in visually high-quality applications. The low color numbers are achieved in particular by the production process according to the invention and the associated steps of working-up (by distillation).

The succinate esters produced according to the invention by the process according to the invention (incl. working-up by distillation and catalyst separation) have especially preferably a low residual acid content, to prevent transesterifications, ester cleavage and/or side reactions (e.g. with stabilizers, additives etc.) especially in complex PVC formulations. In particular, the succinate esters according to the invention have an acid number determined according to DIN EN ISO 2114 of max. 1 mg KOH/g, preferably of max. 0.5 mg KOH/g, especially preferably of max. 0.25 mg KOH/g and quite especially preferably of max. 0.1 mg KOH/g.

The succinate esters according to the invention produced by the process according to the invention (incl. working-up by distillation) have especially preferably a low residual moisture content (water content), to prevent decomposition reactions and/or side reactions. The water content determined according to DIN 51777 is, for the succinate esters according to the invention produced by the process according to the invention, max. 1%, preferably max. 0.5%, especially preferably max. 0.1% and quite especially preferably max. 0.075%.

The purity of the succinate esters according to the invention can be determined according to the prior art by gas chromatography. Moreover, owing to the distribution of isomers in the present case it is necessary to integrate over the peak area of the corresponding peak region. The purity of succinate esters according to the invention produced by the process according to the invention (incl. working-up by distillation) is as a rule >98%, preferably >98.5%, especially preferably >99% and quite especially preferably >99.25%. As a result, clearly identified substances are used exclusively for further processing (e.g. in PVC pastes), which is an advantage especially when assessing toxicology and compatibility phenomena (e.g. exudation phenomena).

Owing to the special structure of the succinate esters according to the invention, molecules are made available that have a rather low density. This is particularly advantageous, because on the one hand during application e.g. in PVC formulations, the plasticizer is added in parts by weight, but on the other hand volumetric phenomena, for example the flow properties, are very relevant especially for the processing of pastes. Thus, the lower the density of a plasticizer is, the more it contributes (simultaneously at low intrinsic viscosity) to lower paste viscosity. The succinate esters according to the invention have a density at 20° C. determined according to DIN 51757 of max. 0.96 g/cm$^3$, preferably of max. 0.95 g/cm$^3$, especially preferably of max. 0.94 g/cm$^3$ and quite especially preferably of max. 0.93 g/cm$^3$.

Compared to the succinate esters based on linear alcohols known from the prior art, the isononyl esters according to the invention have a far lower volatility. Also compared to the succinate esters based on branched alcohols known from the prior art, the isononyl esters according to the invention have better processability and (in many cases) also a lower volatility. Compared to the succinate esters based on 2-ethylhexanol known from the prior art, the isononyl esters according to the invention have for example a much lower volatility from top coat film, and in plastisols a smaller increase in viscosity (thickening factor) over time and therefore improved resistance to aging. The delayed gelling compared to the succinate esters produced on the basis of 2-ethylhexanol provides longer processability at elevated temperatures and can be adapted to the current technical requirements with admixtures of small proportions of a quick-gelling agent, for example alkyl benzoates, pyrrolidone derivatives, citrates etc. The plasticizing action, determined by the Shore "A" hardness determined after 24 h, is only a little lower than with di(2-ethylhexyl)succinate, and the yellowness index and opacity are comparable.

Compared to the succinate esters based on 3,5,5-trimethyl-1-hexanol known from the prior art, the isononyl esters according to the invention have a much lower intrinsic viscosity. In plastisols as well, the viscosity of the diisononyl esters according to the invention is lower, so that the esters according to the invention are eminently suitable for the production of low-viscosity plastisols, especially when blended with other esters. Furthermore, compared to the di-3,5,5-trimethylhexyl succinates known from the prior art, improved gelling and plasticizing action are achieved in or during the production of plastics or compositions of plastics.

Surprisingly, in key properties for the user, the mixtures according to the invention also show improved properties compared to the corresponding phthalate, such as for example much lower intrinsic and paste viscosity, a lower thickening factor (i.e. increase in paste viscosity with storage of the paste e.g. for 2 h, 24 h and 7 days) especially at high shear rates, a much improved thermal stability measured from the increase in the yellowness index YI and the maximum dwell time at the processing temperature (at least 160° C.) until there is black coloration, wherein the plasticizing action defined by the Shore "A" hardness determined after 24 h and the opacity and the yellowness index in top coat recipes are identical at the same plasticizer concentrations.

In addition to the mixtures, compositions are also claimed that comprise these mixtures.

In one embodiment the composition has a polymer selected from polyvinyl chloride, polyvinylbutyral and/or polyalkyl methacrylate.

In one embodiment of the invention, the ratio (parts by weight) of the mixture according to the invention to the polymer is in a range from 1 to 25 to 25 to 1.

In another embodiment of the invention the ratio of the succinate ester mixture according to the invention to other plasticizers not according to the invention is in a range from 1 to 10 to 10 to 1.

The mixtures according to the invention are either used alone, or in mixtures with other plasticizers, for example quick-gelling agents, as compositions, for example in flexible PVC pastes. If they are used together with other plasticizers, the proportion of the succinate esters according to the invention in the plasticizer mixture is at least 5 wt %, preferably at least 15 wt %, especially preferably at least 25 wt % and quite especially preferably at least 30 wt %. This has the advantage that through the targeted use of the succinate esters according to the invention, in particular the paste viscosity of a flexible PVC paste can be lowered in a targeted way.

In a special embodiment the proportion of the mixtures according to the invention in the plasticizer mixture used is at least 50 wt %, especially preferably at least 60 wt % and quite especially preferably at least 70 wt %. This has the advantage that through the targeted use of the succinate esters according to the invention, it is possible in particular to produce PVC pastes with low paste viscosity, whose processing properties, for example gelling, can be adjusted over a wide range by adding further plasticizers, for example quick-gelling agents.

The compounds (plasticizers) differing from the diisononyl esters of succinic acid can be both low-molecular and high-molecular and in particular have both monomeric and polymeric material parameters. For mixtures that contain further esters, these are selected from trialkyl citrates, acylated trialkyl citrates, glycerol esters, epoxidized vegetable oils, saturated or unsaturated fatty acid esters, which can also be partially or fully epoxidized, glycol dibenzoates, alkyl benzoates, dialkyl adipates, trialkyl trimellitates, dialkyl terephthalates, dialkyl phthalates or the dialkyl esters of 1,2-, 1,3- or 1,4-cyclohexane dicarboxylic acids, wherein the alkyl residues have from 4 to 13, preferably 5, 6, 7, 8, 9, 10, 11 or 13 carbon atoms. The plasticizers can also be dianhydrohexitol esters, preferably isosorbide diesters of carboxylic acids, such as n- or iso-butyric acid, valeric acid or 2-ethylhexanoic acid or isononanoic acid.

Polymers that can be contained in the composition according to the invention are e.g. polyvinyl chloride (PVC), polylactic acid (PLA), polyhydroxybutyral (PHB), polyhydroxyvaleric acid (PHV), polyesters, starch, cellulose and cellulose derivatives, especially nitrocellulose (NC), ethyl cellulose (EC), cellulose acetate (CA), cellulose-acetate/butyrate (CAB), polyvinylbutyral (PVB) and the polyalkyl methacrylates (PAMA) and blends or copolymers of the stated polymers. The polymer polyvinyl chloride (PVC) is especially preferred.

Compositions according to the invention are characterized in particular in that the ratio of succinate esters according to the invention to polymer is between 1:25 and 25:1 parts by weight, preferably between 1:20 and 20:1, especially preferably between 1:25 and 10:1 and quite especially preferably between 1:22 and 5:1.

The content of succinate esters according to the invention in the compositions is adjusted according to the particular intended application. Thus, for flexible PVC pastes it is in particular between 5 and 70 parts by weight per 100 parts by weight of PVC, preferably between 7 and 65 parts by weight, especially preferably between 9 and 60 parts by weight and quite especially preferably between 10 and 58 parts by weight, with further subgroups between 10 and 25 parts by weight, between 20 and 35 parts by weight and between 30 and 55 parts by weight.

For dry mixtures, called dryblends, the proportion of the succinate esters according to the invention in the compositions is between 10 and 65 parts by weight per 100 parts by weight of PVC, preferably between 12 and 62 parts by weight, especially preferably between 15 and 60 parts by weight and quite especially preferably between 17 and 58 parts by weight, with further subgroups between 18 and 30 parts by weight, between 25 and 42 parts by weight and between 32 and 56 parts by weight.

In preferred mixtures that contain diisononyl esters of succinic acid and simultaneously plasticizers differing from them structurally, the weight ratio of plasticizers, especially of alkyl benzoates, dialkyl adipates, trialkyl citrates, acylated trialkyl citrates, trialkyl trimellitates, glycol dibenzoates, glycerol esters, dialkyl terephthalates, dialkyl phthalates, dialkanoyl esters of isosorbide and/or the dialkyl esters of 1,2-, 1,3- or 1,4-cyclohexane dicarboxylic acids, to diisononyl succinates is 1 to 10 to 10 to 1, preferably 1 to 5 to 5 to 1.

The formulations or mixtures according to the invention, which contain the succinate esters according to the invention, can also contain further constituents, in addition to polymer(s) and/or other plasticizers or esters. These further constituents are selected in particular from pigments, fillers, solvents, stabilizers, costabilizers (e.g. epoxidized vegetable oils), rheology additives, flatting agents, blowing agents, decomposition catalysts, deaerating additives, fungicides and flame retardants.

The present invention also relates to products that contain the succinate esters according to the invention, especially PVC-based floor coverings, PVC-based wall coverings (e.g. wallpapers) and hoses, films, semifinished products, finished products and PVC-based awnings. Through the use of the succinate esters according to the invention, in particular these products have especially favorable processing properties or, owing to the proportion of renewable raw materials in the succinate esters according to the invention that are used, in particular they have improved environmental indices (e.g. $CO_2$ balance).

In a particular embodiment, the films according to the invention are packaging films, especially those that are used for the packaging of foodstuffs, wherein in particular the good toxicological properties of the succinate esters according to the invention are advantageous.

In addition to the mixtures, uses thereof are also claimed.

In another particular embodiment, the films that contain the mixtures according to the invention are used for producing storage bags for body fluids (especially blood or urine), wherein in particular the good toxicological properties of the mixtures according to the invention are advantageous.

In another particular embodiment, the semifinished products or finished products are components of children's toys, which are characterized in particular by their good toxicological properties. When using the mixtures according to the invention in compositions that are used for producing children's toys, the combination of the mixtures according to the invention with stabilizers that do not contain any heavy metals is especially preferred.

In another particular embodiment, the semifinished products or finished products are products that are used for the medical care of humans and/or animals (e.g. breathing masks, tubes, catheter connections etc.), wherein in particular the good sterilizability of the products and the good toxicological properties of the mixtures according to the invention are advantageous.

The use of the composition according to the invention is also claimed.

Preferably the composition according to the invention is used as plasticizer.

In one embodiment, the composition is used as plasticizer in the production of paints, inks, adhesives or components of adhesives, varnishes, plastisols, resists and/or sealants.

In one embodiment the composition is used as solvent in the production of paints, inks, adhesives or components of adhesives, varnishes, plastisols, and/or sealants.

In one embodiment the composition is used as a component of lubricating oil.

In one embodiment the composition is used as an aid in metalworking.

The present invention further relates to the use of the mixtures according to the invention and of compositions that contain the mixtures according to the invention.

The mixtures or the composition can be used in or as paints, ink(s) or varnish(es), in plastisol(s), adhesive(s) or component(s) of adhesives, in sealants, in or as plasticizer(s) for plastics or plastic components, as solvents, as components of lubricating oil and as aids in metalworking.

ANALYSIS

1. Determination of the Content of 3,5,5-Trimethylhexanol and n-Nonanol Via Determination of Isomers by Gas Chromatography (GC)

Determination of the content of 3,5,5-trimethylhexanol and n-nonanol in the mixture of branched nonyl alcohols (=isononanol) used for preparing the esters according to the invention by gas chromatography (GC) was carried out with a Hewlett Packard "HP 5896" automatic gas chromatograph using a DB-FFAP column (length: 30 m, inside diameter: 0.25 mm, film thickness 0.25 µm) from Agilent and a flame ionization detector with the following basic conditions:
GC furnace temperature: 145° C. Injector temperature: 250° C.
Detector temperature: 250° C.
Total run time: 50 minutes
Carrier gas: helium (1 bar) Split flow: 100 ml/min
Injection volume: 0.2 µl The GC signals were ascribed to the two isomers on the basis of run time comparisons with appropriate comparative substances.

2. Determination of Ester Purity by Gas Chromatography (GC)

The purity of the esters produced is determined by GC with a "6890N" automatic gas chromatograph from Agilent Technologies using a DB-5 column (length: 20 m, inside diameter: 0.25 mm, film thickness 0.25 µm) from J&W Scientific and a flame ionization detector with the following basic conditions:
Initial temperature of furnace: 150° C. Final temperature of furnace: 350° C.
(1) Heating rate 150-300° C.: 10 K/min (2) Isothermal: 10 min at 300° C.
(3) Heating rate 300-350° C.: 25 K/min.
Total run time: 27 min.
Inlet temperature of injection block: 300° C. Split ratio: 200:1
Split flow: 121.1 ml/min Total flow: 124.6 ml/min.
Carrier gas: helium Injection volume: 3 microliters
Detector temperature: 350° C. Fuel gas: hydrogen
Hydrogen flow rate: 40 ml/min. Air flow rate: 440 ml/min.
Makeup gas: helium Flow rate of makeup gas: 45 ml/min.

The gas chromatograms obtained are evaluated manually against existing comparative substances and the purity is stated as percentage area. Owing to the high final contents of target substance of >99.4%, the expected error through absence of calibration for the respective sample substance is small.

3. Determination of APHA Color Number

The color number of the esters produced was determined according to DIN EN ISO 6271-2.

4. Determination of Density

The density of the esters produced is determined by means of a flexural resonator according to DIN 51757—Method 4.

5. Determination of the Acid Number

The acid number of the esters produced is determined according to DIN EN ISO 2114.

6. Determination of Water Content

The water content of the esters produced is determined according to DIN 51777 Part 1 (Direct Method).

7. Determination of the Intrinsic Viscosity of the Carboxylates

The intrinsic viscosity (shear viscosity) of the esters produced is determined using a Physica MCR 101 (from Anton-Paar) with Z3 measuring system (DIN 25 mm) in rotation mode by the following method:
Esters and measuring system were first temperature-controlled to a temperature of 20° C., then the following points were controlled:
1. A preliminary shearing of 100 s$^{-1}$ for a period of 60 s, in which no measured values were recorded (for evening out any thixotropic effects and for better temperature distribution).
2. A downward frequency ramp, beginning at 500 s$^{-1}$ and ending at 0.1 s$^{-1}$, divided up into a logarithmic series with 20 steps with in each case 5 s measurement point duration (verification of Newtonian behavior).

All esters displayed Newtonian flow behavior. The viscosity values were stated as examples at a shear rate of 1 s$^{-1}$.

8. Determination of Mass Loss after 10 Minutes at 200° C.

The mass loss at 200° C. of the esters produced was determined using a halogen dryer of type "HB43S" (from Mettler). The following measurement parameters were set:
Temperature ramp: constant 200° C.
Measured value recording: 30 s
Measurement time: 10 min
Sample quantity: 5 g Disposable aluminum dishes (from Mettler) and HS 1 fiber filters (glass-fiber mat from Mettler) were used for measurement. After leveling and calibration of the balance, the samples (5 g) were distributed uniformly on the fiber filter and measurement was started. Determination in duplicate was carried out for each sample, and the measured values were averaged. The last measured value after 10 min is given as "Mass loss after 10 minutes at 200° C.".

9. Thermal Analysis Procedure and Evaluation (DSC and TGA)

The enthalpy of fusion and the glass transition temperature are determined by differential calorimetry (DSC) according to DIN 51007 (temperature range from −100° C. to +200° C.) from the first heating curve at a heating rate of 10 K/min. The turning point of the heat flow curve is evaluated as the glass transition temperature. The enthalpy of fusion is determined by integration of the peak area(s).

Thermogravimetric measurement (TGA) was carried out according to DIN 51006 (temperature range: 25° C. to 310° C.) at a heating rate of 10 K/min.

10. Determination of Plastisol Viscosity

The viscosity of the PVC plastisols was measured using a Physica MCR 101 (from Anton-Paar), using the rotation mode and the "Z3" measuring system (DIN 25 mm).

The plastisol was first homogenized manually in the preparation vessel with a spatula, then filled in the measuring system and measured isothermally at 25° C. The following points were controlled during the measurement:
1. A preliminary shearing of 100 s$^{-1}$ for a period of 60 s, in which no measured values were recorded (for evening out any thixotropic effects).
2. A downward frequency ramp, beginning at 200 s$^{-1}$ and ending at 0.1 s$^{-1}$, divided up into a logarithmic series with 30 steps each with measurement point duration of 5 seconds.

As a rule (unless stated otherwise), the measurements were carried out after storage/maturation of the plastisols for 24 h (at 25° C.).

11. Determination of the Gelling Rate

The gelling behavior of the plastisols was investigated in the Physica MCR 101 in oscillation mode with a plate/plate measuring system (PP25), which was operated with controlled shear stress. An additional temperature-control hood was connected to the equipment, to obtain optimal heat distribution.
Measurement Parameters:
Mode:
Temperature-gradient (temperature ramp)
Start temperature: 25° C.
End temperature: 180° C.
Heating/cooling rate: 5 K/min
Oscillation frequency: 4-0.1 Hz ramp (logarithmic)
Angular frequency omega: 10 l/s
Number of measurement points: 63
Measurement point duration: 0.5 min
Automatic gap tracking F: 0 N
Constant measurement point duration
Gap width 0.5 mm
Measurement Procedure:

A drop of the plastisol recipe to be measured, free from air bubbles, was deposited on the lower plate of the measuring system. Care was taken that after bringing the measuring system together, some plastisol could bulge uniformly out of the measuring system (not more than approx. 6 mm all around). Then the temperature-control hood was positioned above the sample and the measurement was started.

The so-called complex viscosity of the plastisol was determined as a function of the temperature. The start of the gelling process was detected from a sudden sharp increase in the complex viscosity. Earlier occurrence of this increase in viscosity meant better gelling capacity of the system.

From the measured curves obtained, the temperatures at which a complex viscosity of 1000 Pa·s or 10 000 Pa*s was reached were determined by interpolation for each plastisol. In addition, the tangential method was used for determining the maximum plastisol viscosity reached in the present test setup, and the temperature starting from which the maximum plastisol viscosity occurs was found by dropping a perpendicular.

12. Determination of the Yellowness Index on Foam and Top Coat Films

The yellowness index (index YD 1925) is a measure of the yellowing of a test specimen. The measurement of color was carried out with a "Spectro Guide" instrument from Byk-Gardner. A white reference tile was used as background for the color measurements. The following parameters were set:
Type of light: C/2°
Number of measurements: 3
Reading: CIE L*a*b*
Measured index: YD1925

The measurements themselves were carried out at 3 different points of the samples (for special-effect and finishing foams at a plastisol knife-application thickness of 200 μm). The values from the 3 measurements were averaged.

13. Determination of Shore Hardness (Plasticizer Efficiency)

The hardness measurements were carried out according to DIN 53 505 with a Shore A measuring instrument from Zwick-Roell, in each case reading the measured value after 3 seconds. For each test specimen (e.g. casting), measurements were taken at three different points, and the mean value was found.

14. Determination of the Opacity of Top Coat Films

The opacity was determined with a "Spectro Guide" instrument from Byk Gardner. A white tile and a black tile were used as background for the opacity measurements. Opacity measurement was selected from the menu on the colorimeter. The measurements themselves were taken at 3 different points of the samples and were evaluated automatically.

EXAMPLE 1

Analysis of the Isononyl Alcohol Used for Preparing the Succinate Esters, with Respect to the Content of 3,5,5-trimethylhexanol and n-nonanol The distribution of isomers was determined by GC with the method described in Analysis, Point 1. The results are presented in Table 1.

TABLE 1

| | Distribution of isomers | | | | | |
|---|---|---|---|---|---|---|
| | 3,5,5-Trimethylhexanol [wt %] | n-Nonanol [wt %] | Alcohols with more than 9 carbon atoms [wt %] | Alcohols with less than 9 carbon atoms [wt %] | Proportion of alcohols with 1 methyl branching on the β-carbon atom [wt %] | Proportion of alcohols with 2 methyl branchings on the β-carbon atom [wt %] |
| VESTINOL 9 | 0.03 | 7.6 | <1 | <1 | 15.8 | <1 |
| Exxal 9 | 0.11 | 1.3 | 24.8 | 2.5 | 18.67 | <1 |
| Exxal 9 S | 0.13 | 1.5 | 4.7 | 1.6 | 18.85 | <1 |

EXAMPLE 2

Preparation of the Carboxylates 2.1 Preparation of Diisononyl Adipate (DINA) from Adipic Acid and Isononanol from the Company Evonik Oxeno GmbH (Comparative Test)

A 4-liter stirred flask with a device for removing water, a surmounted high-efficiency condenser, stirrer, plunge pipe, dropping funnel and thermometer was charged with 730 g (5 mol) of adipic acid (from Sigma Aldrich), 0.44 g (0.06 wt % relative to adipic acid) of tetrabutyl orthotitanate (Vertec TNBT, from Johnson Matthey Catalysts) and 1872 g (13 mol) of an isononanol prepared by the OCTOL process (from Evonik Oxeno GmbH), and it was esterified at up to 240° C. The reaction was stopped after 3 hours. Then the excess alcohol was distilled off up to 180° C. and 3 mbar. Then it was cooled to 80° C. and was neutralized with 17 ml of 10 wt % aqueous NaOH solution. Next, steam distillation was carried out at a temperature of 180° C. and a pressure between 20 and 5 mbar. Then the mixture was cooled to 130° C. and was dried at this temperature at 5 mbar. After cooling to <100° C. the mixture was filtered through a filter aid. GC showed an ester content (purity) of >99.9%.

2.2 Preparation of di-2-ethylhexyl succinate (D2EHS) from succinic acid and 2-ethylhexanol (Comparative Test)

A 4-liter stirred flask fitted with a device for removing water, a surmounted high-efficiency condenser, stirrer, plunge pipe, dropping funnel and thermometer was charged with 826 g (7 mol) of succinic acid (from Sigma Aldrich), 2.07 g (0.25 wt % relative to succinic acid) of tetrabutyl orthotitanate (Vertec TNBT, from Johnson Matthey Catalysts) and 2210 g (17 mol) of 2-ethylhexanol (from Sigma Aldrich), and it was esterified at up to 220° C. The reaction was stopped after 3 hours. Then the excess alcohol was distilled off at up to 180° C. and 3 mbar. Then it was cooled to 80° C. and it was neutralized with 7.5 ml of 10 wt % aqueous NaOH solution. Then the mixture was purified at a temperature of 140° C. and a pressure of 40 mbar by passing nitrogen through it. Then the mixture was cooled to 90° C. and it was lightened at this temperature by adding 11.5 g (0.5% relative to the remaining amount of ester) of activated charcoal (CAP Super from Norit). Then the mixture was filtered at <90° C. through a filter aid (perlite). GC showed an ester content (purity) of 99.46%.

2.3 Preparation of Diisononyl Succinate (DINS) from Succinic Acid and Isononanol from the Company Evonik Oxeno GmbH (According to the Invention)

A 4-liter stirred flask fitted with a device for removing water, a surmounted high-efficiency condenser, stirrer, plunge pipe, dropping funnel and thermometer was charged with 826 g (7 mol) of succinic acid (from Sigma Aldrich), 2.07 g (0.25 wt % relative to succinic acid) of tetrabutyl orthotitanate (Vertec TNBT, from Johnson Matthey Catalysts) and 2448 g (17 mol) of an isononanol prepared by the OCTOL process (from Evonik Oxeno GmbH) and it was esterified at up to 220° C. The reaction was stopped after 3 hours. Then the excess alcohol was distilled off at 180° C. and 3 mbar. Then it was cooled to 80° C. and it was neutralized with 2 ml of 10 wt % aqueous NaOH solution. Then the mixture was purified at a temperature of 160° C. and a pressure of 40 mbar by passing nitrogen through it. Then the mixture was cooled to 90° C. and it was lightened at this temperature by adding 11.5 g (0.5% relative to the remaining amount of ester) of activated charcoal (CAP Super from Norit). Then the mixture was filtered through a filter aid at <90° C. GC showed an ester content (purity) of 99.84%. Characteristic material parameters for the esters obtained in example 2 are presented in Table 2.

EXAMPLE 3

Examples of Formulations Containing the Succinate Esters According to the Invention In the following, the succinate esters according to the invention are used in general PVC formulations, to illustrate the range of uses of the esters according to the invention. The formulations presented below can or must be adapted by a person skilled in the art to the specific processing and usage requirements in the respective fields of application.

3.1 Transparent Top Coat (Floor Covering)
- 64.5 parts by weight of suspension PVC with a K value (according to DIN EN ISO 1628-2) of 60-75 (e.g. VESTOLIT B 7021-Ultra)
- 32.3 parts by weight of succinate esters according to the invention according to example 2.3
- 1.9 parts by weight of epoxidized soybean oil as (co)stabilizer (e.g. DRAPEX 39)
- 1.3 parts by weight of stabilizer (e.g. MARK C/Z 149)

Preparation of the Plastisol

The plastisol was prepared using a Kreiss Dissolver VDKV30-3 (from Niemann). The liquid ingredients of the recipe were weighed in a mixing beaker before the solid ingredients. The mixture was stirred by hand with a salve spatula so that there was no longer any unwetted powder. The mixing beaker was then clamped in the clamping device of the dissolver stirrer. The sample was homogenized using the appropriate mixer disk (D: 50 mm). During homogenization, a vacuum was created in the mixing vessel by means of a vacuum pump. The pressure in the mixing vessel was monitored with a vacuummeter (DVR 2 from Vakuubrand). A pressure (abs.) of under 10 mbar was reached.

Moreover, the rotary speed was increased from 330 rev/min to 2000 rev/min, and stirring was continued until the temperature on the digital display of the temperature sensor reached 30° C. This ensured that the homogenization of the plastisol was achieved with a defined energy input. Then the plastisol was stirred for a further 10 min at a rotary speed of 330 rev/min and deaerated. Following preparation of the plastisol, it was immediately attemperated at 25° C.

TABLE 2

Material parameters of the carboxylates

| Product (according to example) | Purity (GC) [FI-%] | Degree of branching (NMR) [—] | APHA color [—] | Density [g/cm³] | Acid number [mg KOH/g] | Water content [%] | Intrinsic viscosity [mPa*s] | Mass loss TGA up to 300° C. [%] | Mass loss after 10 minutes @200° C. [wt %] | DSC $T_g$ [° C.] | DSC $\Delta H_M$ [J/g] |
|---|---|---|---|---|---|---|---|---|---|---|---|
| Di(isononyl)phthalate, VESTINOL ® 9, from Evonik Oxeno GmbH (comparative example) | 99.95 | 1.29 | 5 | 0.9741 | 0.016 | 0.023 | 76 | 7.5 | 3.7 | −86 | 0 |
| Di(isononyl)adipate according to example 2.1 (comparative example) | 99.9 | n.d. | 8 | 0.9216 | 0.019 | 0.01 | 19 | 21.1 | 7.3 | −106 | 19.2 |
| Di(2-ethylhexyl)succinate according to example 2.2 (comparative example) | 99.46 | n.d. | 4 | 0.932 | 0.03 | 0.02 | 13 | 34.8 | 28.9 | −103 | 0 |
| Di(isononyl)succinate according to example 2.3 (according to the invention) | 99.84 | n.d. | 18 | 0.9269 | 0.02 | 0.005 | 18 | 14.5 | 13.8 | −104 | 0 | n.d. = not determined

Preparation of the Films

As a rule the films are prepared after a maturation time of 24 hours (at 25° C.). For production of the films, a knife gap of 1.40 mm was set on the roll knife of a Mathis Labcoater (manufacturer: W. Mathis AG). This was checked with a feeler gauge and adjusted if necessary. The plastisols produced were knife-coated on high-gloss paper (Ultracast Patent; from Sappi Ltd.) clamped flat in a frame, by means of the roll knife of the Mathis Labcoater. The knife-coated plastisol was now gelled for 2 min in the Mathis stove at 200° C. After cooling, the film thickness was determined using a quick thickness measuring instrument (KXL047; from Mitutoyo) with an accuracy of 0.01 mm. At the stated knife gap, the film thickness of this film was in all cases between 0.95 and 1.05 mm. The thickness was measured at three different points of the film.

3.2 Backing Foam (Floor Covering)

- 61.5 parts by weight PVC with a K value (according to DIN EN ISO 1628-2) of 65-75 (e.g. VINNOLIT MP 6852)
- 36 parts by weight succinate esters according to the invention according to example 2.3
- 1.5 parts by weight thermally activatable blowing agent (e.g. based on azodicarbonamide)
- 1 part by weight zinc oxide Preparation of the Plastisol The plastisols were prepared as described in example 3.1, but using the recipe given in example 3.2.

Production of the Films

As a rule the films were produced after a plastisol maturation time of 24 hours (at 25° C.). For film production, a knife gap of 1.00 mm was set on the roll knife of a Mathis Labcoater (manufacturer: W. Mathis AG). This was checked with a feeler gauge and adjusted if necessary. The plastisols produced were knife-coated on a release paper clamped flat in a frame (Warren Release Paper—Stripcote EHR; from Sappi Ltd.) by means of the roll knife of the Mathis Labcoater. The knife-coated plastisol was now gelled for 30 s in the Mathis stove at 200° C. After cooling, the film thickness was determined using a quick thickness measuring instrument (KXL047; from Mitutoyo) with an accuracy of 0.01 mm. At the stated knife gap, the film thickness of this film was in all cases between 0.74 and 0.77 mm. The thickness was measured at three different points of the film. Then the foamed films (foams) were also produced at different oven residence times (e.g. 60 s, 90 s, 120 s and 150 s) with the or in the Mathis-Labcoater.

3.3 Foam Layer for Coating (Floor Covering)

- 35 parts by weight PVC with a K value (according to DIN EN ISO 1628-2) of 65-75 (e.g. VESTOLIT P 1352 K)
- 24.5 parts by weight succinate esters according to the invention according to example 2.3
- 35 parts by weight calcium carbonate (e.g. Calcilit 8 G)
- 2.5 parts by weight titanium dioxide (e.g. Kronos 2220)
- 1 part by weight thermally activatable blowing agent (e.g. based on azodicarbonamide)
- 1 part by weight zinc oxide
- 1 part by weight isopropanol Production of the Plastisol The plastisols were prepared as described in example 3.1, but using the recipe given in example 3.3.

Preparation of the Film

The films were produced as described in example 3.2, but using a plastisol produced according to example 3.3.

3.4 Floor Covering, Calendered (Dryblend)

- 65 parts by weight of suspension PVC with a K value (according to DIN EN ISO 1628-2) of 65-75 (e.g. SolVin 271 PC)
- 31 parts by weight succinate esters according to the invention according to example 2.3
- 0.5 parts by weight stabilizer (e.g. metal-free organic stabilizer such as Mark OBS 1100)
- 1 part by weight stabilizer (e.g. metal-free organic stabilizer such as Mark OBS 1360)
- 2 parts by weight epoxidized soybean oil as (co)stabilizer (e.g. DRAPEX 39)
- 0.5 parts by weight calcium stearate (as processing aid/lubricant)

Preparation of the Dryblends

The dryblends were prepared in a Brabender planetary mixer. The mixing vessel of the planetary mixer was controlled to a constant temperature of 90° C. Using software, the following parameters were set on the planetary mixer.

Rotary speed program: yes
Profile: rotary speed 50 rev/min; holding time 9 min; increase time 1 min
Rotary speed 100 rev/min; holding time 20 min
Kneader temperature: 88° C.
Measurement range: 2 Nm
Damping: 3

Through heat losses that occurred, the temperature in the mixing vessel reached 88° C. After the planetary mixer had undergone a self-calibration, the solid ingredients were fed via a funnel to the mixing vessel. The program was started and the powder mixture was stirred for 10 minutes in the mixing vessel, before the liquid ingredients were added. The liquid ingredients were pre-weighed. The mixture was now stirred for a further 20 minutes in the planetary mixer. On completion of the program, the prepared dryblend was taken out and at room temperature. The torque-time diagram was evaluated by the software. Following addition of the liquid ingredients there is a marked rise of the curve. Plasticizer uptake is not completed until the curve shows a marked decrease again. The time difference of these two points is the plasticizer uptake time (dryblend time). The maximum torque is evaluated automatically by the program.

Processing of the Dryblends
Preparation of the Rolled Sheets

The rolled sheets were produced on a W150 AP calender from the company Collin.

The following parameters were set for this on the calender:
Roll temperature: 165° C.
Roll gap: 0.5 mm
Rolling time: 5 min Five-Step Program for Production of Rolled Sheet After reaching the roll temperature, the roll gap was calibrated. At the start of measurement the roll gap was set at 0.2 mm. The dryblend was weighed-in in one (as a rule approx. 160 g total mass) and was put in the roll gap with the rolls stationary. The program was started. The rolls started with a rotary speed of 5 rev/min and a friction of 20%. After approx. 1 min, plasticization was largely completed and the roll gap was increased to 0.5 mm. Three-fold homogenization was carried out by means of an automatic transfer unit on the calender. After 5 min the rolled sheet was removed from the roll and cooled.

Preparation of the Pressed Boards

The pressed boards were produced on a laboratory press from the company Collin. The previously prepared rolled sheets (see above) were used for making the pressed boards. The lateral edges of the rolled sheets were removed with a cutting machine, and the rolled sheet was then cut into pieces of approx. 14.5×14.5 cm. For 1 mm thick pressed boards, in each case 2 pieces of rolled sheet were laid in the 15×15 cm pressing frame made of special steel.

The following parameters were set on the laboratory press:
Three-phase program:
Phase 1: both boards 165°; pressed board pressure: 5 bar; phase time: 60 seconds.
Phase 2: both boards 165°; pressed board pressure: 200 bar; phase time: 120 seconds.
Phase 3: both boards 40°; pressed board pressure: 200 bar; phase time: 270 seconds.

The excess press lip was removed after production of the pressed boards.

3.5 Wallpaper Recipe, Bouclé-Foam (Special-Effect Foam)
- 48 parts by weight PVC with a K value (according to DIN EN ISO 1628-2) of 65-75 (e.g. VESTOLIT E 7012 S)
- 26 parts by weight succinate esters according to the invention according to example 2.3
- 2.5 parts by weight thermally activatable blowing agent (e.g. based on azodicarbonamide)
- 15 parts by weight calcium carbonate (e.g. Calcilit 8 G)
- 4 parts by weight titanium dioxide (e.g. Kronos 2220)
- 1.5 parts by weight decomposition catalyst/"Kicker" K/Zn-based (e.g. Baerostab KK 48)
- 1.5 parts by weight paraffinic solvent (e.g. Isopar J)
- 1.5 parts by weight isopropanol Preparation of the Plastisols The plastisols were produced using a "Eurostar" laboratory stirrer (from IKA). A toothed mixer disk with a diameter of 50 mm was mounted on the stirrer. Before the solid ingredients, the liquid ingredients of the recipe were weighed in a PE mixing beaker on a balance (Mettler XS6002S). The mixture was stirred by hand with a salve spatula so that there was no longer any unwetted powder. The laboratory stirrer was then immersed in the mixture and the rotary speed of the stirrer was increased within 15 s from 0 to 2000 rev/min. The mixture was homogenized at a rotary speed of 2000 rev/min for a further 45 s, so that the mixing time for all plastisols was 60 s. After the plastisol was prepared, it was immediately attemperated at 25.0° C.

Processing of the Plastisols/Production of the Wallpaper Foams

After a storage time of at least two hours and max. 24 hours, the plastisols were foamed in a Mathis oven (type LTE-TS). A coated wallpaper paper (from Ahlstrom GmbH) was selected as carrier. The plastisols were applied in 3 different thicknesses (300 μm, 200 μm and 100 μm) with a knife-coating unit. In each case 3 plastisols were coated next to one another. The plastisols were fully foamed at 3 different temperatures (200° C., 210° C. and 220° C.) with a residence time of 60 seconds. After the foams had cooled, the wallpapers were trimmed for further processing.

3.6 Wallpaper Recipe, Smooth Foam
- 18 parts by weight PVC with a K value (according to DIN EN ISO 1628-2) of 65-75 (e.g. VESTOLIT E 7012 S)
- 16 parts by weight emulsion PVC with a K value (according to DIN EN ISO 1628-2) of 65-75 (e.g. VINNOLIT E 67 ST)
- 13.5 parts by weight microsuspension PVC with a K value (according to DIN EN ISO 1628-2) of 55-67 (e.g. VESTOLIT B 6021-Ultra)
- 25 parts by weight succinate esters according to the invention according to example 2.3
- 1.5 parts by weight thermally activatable blowing agent (e.g. based on azodicarbonamide)
- 3 parts by weight epoxidized soybean oil as (co)stabilizer (e.g. DRAPEX 39)
- 2 parts by weight titanium dioxide (e.g. Kronos 2220)
- 20 parts by weight calcium-magnesium carbonate (e.g. Microdol A 1)
- 1 part by weight decomposition catalyst/"Kicker" K/Zn-based (e.g. Baerostab KK 48)

Preparation of the Plastisols

The plastisols were produced as described in example 3.5, but using the recipe given in example 3.6.

Preparation of the Film

The wallpapers were produced as described in example 3.5, but using a plastisol produced according to example 3.6.

3.7 Wallpaper Recipe, Compact-Matt
- 28 parts by weight PVC with a K value (according to DIN EN ISO 1628-2) of 65-75 (e.g. VESTOLIT E 7012 S)
- 26 parts by weight succinate esters according to the invention according to example 2.3
- 37 parts by weight precipitated uncoated calcium carbonate (e.g. SOCAL N2R)
- 4.5 parts by weight titanium dioxide (e.g. Kronos 2220)
- 3 parts by weight epoxidized soybean oil as (co)stabilizer (e.g. DRAPEX 39)
- 1.5 parts by weight stabilizer (e.g. Mark B/Z 562)

Preparation of the Plastisols

The plastisols were produced as described in example 3.5, but using the recipe given in example 3.7.

Preparation of the Film

The wallpapers were produced as described in example 3.5, but using a plastisol produced according to example 3.7.

3.8 PVC Awnings, Coating Mass
- 55 parts by weight PVC with a K value (according to DIN EN ISO 1628-2) of 65-75 (e.g. VESTOLIT P 1430 K70)
- 33 parts by weight succinate esters according to the invention according to example 2.3
- 8 parts by weight calcium carbonate (e.g. Calcilit 8 G)
- 1.5 parts by weight titanium dioxide (e.g. Kronos 2220)
- 1.5 parts by weight epoxidized soybean oil as (co)stabilizer (e.g. DRAPEX 39)
- 1 part by weight stabilizer (e.g. MARK B/Z 561)

Preparation of the Plastisol

The plastisols were produced as described in example 3.1, but using the recipe given in example 3.8.

Preparation of the Film

The awnings were produced as described in example 3.1, but using a plastisol produced according to example 3.8.

3.9 PVC Roofing Sheet
- 65 parts by weight suspension PVC with a K value (according to DIN EN ISO 1628-2) of 65-75 (e.g. SolVin 271PC)
- 31.5 parts by weight succinate esters according to the invention according to example 2.3
- 2 parts by weight epoxidized soybean oil as (co)stabilizer (e.g. DRAPEX 39)
- 1 part by weight stabilizer (e.g. MARK B/Z 561)
- 0.5 parts by weight calcium stearate Preparation of the Dryblend The dryblends were produced as described in example 3.4, but using the recipe given in example 3.9.

Preparation of the Pressed Boards

The pressed boards were produced as described in example 3.4, but using a dryblend produced according to example 3.9.

3.10 PVC Hose Recipe (Filled)
- 65 parts by weight suspension PVC with a K value (according to DIN EN ISO 1628-2) of 65-75 (e.g. SolVin 271PC)
- 20 parts by weight succinate esters according to the invention according to example 2.3
- 12.5 parts by weight calcium carbonate (e.g. Omya EXH1-OM)
- 1.5 parts by weight titanium dioxide (e.g. Kronos 2220)

0.5 parts by weight stabilizer (e.g. Baerostab MC 8763-1 CP)
0.5 parts by weight lubricant based on fatty acid ester (e.g. Loxiol G 40)

Preparation of the Dryblend

The dryblends were produced as described in example 3.4, but using the recipe given in example 3.10.

Preparation of the Pressed Boards

The pressed boards were produced as described in example 3.4, but using a dryblend produced according to example 3.10.

3.11 Cable Sheathing
  46.5 parts by weight suspension PVC with a K value (according to DIN EN ISO 1628-2) of 65-75 (e.g. SolVin 271 PC)
  29 parts by weight succinate esters according to the invention according to example 2.3
  23 parts by weight calcium carbonate (e.g. OMYA BSH)
  1.5 parts by weight stabilizer (e.g. Baeropan MC KA 83/5)

Preparation of the Dryblend

The dryblends were produced as described in example 3.4, but using the recipe given in example 3.11.

Preparation of the Pressed Boards

The pressed boards were produced as described in example 3.4, but using a dryblend produced according to example 3.11.

3.12 Cable Insulation Compound
  43 parts by weight suspension PVC with a K value (according to DIN EN ISO 1628-2) of 65-75 (e.g. SolVin 271PC)
  21 part by weight succinate esters according to the invention according to example 2.3
  34 parts by weight calcium carbonate (e.g. OMYA BSH)
  2 parts by weight stabilizer (e.g. Baeropan MC KA 83/5)

Preparation of the Dryblend

The dryblends were produced as described in example 3.4, but using the recipe given in example 3.12.

Preparation of the Pressed Boards

The pressed boards were produced as described in example 3.4, but using a dryblend produced according to example 3.12.

3.13 Resist (UBS)
  32 parts by weight suspension PVC with a K value (according to DIN EN ISO 1628-2) of 65-75 (e.g. VESTOLIT E7031)
  41 part by weight succinate esters according to the invention according to example 2.3
  21.5 parts by weight coated calcium carbonate (e.g. SOCAL 312)
  2 parts by weight (white) lime powder/quicklime (e.g. PRECAL 30S)
  1 part by weight adhesion promoter (e.g. Nouribond 323; from Air Products)
  0.5 parts by weight zinc oxide (e.g. active zinc oxide)
  2 parts by weight aliphatic solvent with boiling point >180° C. (e.g. Shellsol D70)

Preparation of the Plastisol

The plastisols were produced as described in example 3.1, but using the recipe given in example 3.13.

In the following, the succinate esters according to the invention are used in selected PVC formulations, and are investigated extensively with respect to the material, processing and product properties, in order to demonstrate the obtainable advantages in detail. The formulations presented below are also generally adopted, and can/must be adapted by a person skilled in the art to the specific processing and usage requirements in the respective fields of application.

EXAMPLE 4

Use of Diisononyl Esters of Succinic Acid (Diisononyl Succinates) in PVC Top Coat Formulation (Plastisol)—Production of the Top Coat Plastisols The following formulation is an example of the use of the succinate esters according to the invention in transparent top coat layers, such as are used e.g. in the production of (multi-layer) PVC floor coverings. The plastisols were prepared according to example 3.1, but with an amended recipe. The initial weights of the ingredients used for the various plastisols are shown in the following Table 3.

TABLE 3

PVC top coat recipes
[all information in phr (=parts by weight per 100 parts by weight PVC)]

| Plastisol recipe | 1** | 2** | 3** | 4* |
|---|---|---|---|---|
| Vestolit B 7021 - Ultra | 100 | 100 | 100 | 100 |
| VESTINOL ® 9 | 50 | | | |
| Di(isononyl)adipate according to Ex. 2.1 | | 50 | | |
| Di(2-ethylhexyl)succinate according to Ex. 2.2 | | | 50 | |
| Di(isononyl)succinate according to Ex. 2.3 | | | | 50 |
| Drapex 39 | 3 | 3 | 3 | 3 |
| Mark CZ 149 | 2 | 2 | 2 | 2 |

**= comparative example
*= according to the invention

The materials and substances used are explained in more detail below:

Vestolit B 7021-Ultra: Microsuspension PVC (homopolymer) with a K value (determined according to DIN EN ISO 1628-2) of 70; from Vestolit GmbH.
VESTINOL® 9: Diisononyl(ortho)phthalate (DINP), plasticizer; from Evonik Oxeno GmbH.
Drapex 39: Epoxidized soybean oil; costabilizer with plasticizing action; from Chemtura/Galata Chemicals.
Mark CZ 149: Calcium/zinc stabilizer; from Chemtura/Galata Chemicals.

EXAMPLE 5

Determination of the Plastisol Viscosity of the Top Coat Plastisols Containing Diisononyl Succinates after a Storage Time of 24 h (at 25° C.)

The viscosities of the plastisols produced in example 4 were measured with a Physica MCR 101 rheometer (from Paar-Physica), according to the procedure described under Analysis, Point 11. The results are shown in the following Table 4 for example for shear rates of 100/s, 10/s, 1/s and 0.1/s.

TABLE 4

Shear viscosity of the plastisols from example 4 after 24 h storage at 25° C.

| Plastisol recipe according to Ex. 4 | 1** | 2** | 3** | 4* |
|---|---|---|---|---|
| Shear viscosity at shear rate = 100/s [Pa * s] | 6.8 | 1 | 0.7 | 1 |
| Shear viscosity at shear rate = 10/s [Pa * s] | 3.2 | 0.63 | 0.46 | 0.58 |

TABLE 4-continued

Shear viscosity of the plastisols from example 4
after 24 h storage at 25° C.

| Plastisol recipe according to Ex. 4 | 1** | 2** | 3** | 4* |
|---|---|---|---|---|
| Shear viscosity at shear rate = 1/s [Pa * s] | 2.8 | 0.65 | 0.48 | 0.58 |
| Shear viscosity at shear rate = 0.1/s [Pa * s] | 3.19 | 0.82 | 0.63 | 0.73 |

**= comparative example
*= according to the invention
n. db. = not determinable

Compared to the DINP standard plastisol (1), all other plastisols have a much lower shear viscosity, and—as to be expected—it is slightly higher for the plastisol according to the invention (4) than for the similar plastisol based on di(2-ethylhexyl)succinate. Thus, plastisols according to the invention are made available, which have a very low plastisol viscosity and as a result possess much better processability than the known DINP plastisols. In comparison with the plastisols also known based on di(isononyl adipate), the easier accessibility from renewable raw materials and the price advantage of succinic acid versus adipic acid may be mentioned as advantages for the plastisols according to the invention. The far lower plastisol viscosity also offers a person skilled in the art the possibility of greatly reducing the total amount of plasticizer through corresponding adjustments of the recipe.

EXAMPLE 6

Determination of the Gelling Behavior of the PVC Top Coat Plastisols Produced in Example 4

The gelling behavior of the PVC top coat plastisols produced in example 4 was investigated as described under Analysis, Point 12 (see above), with a Physica MCR 101 in oscillation mode after storing the plastisols at 25° C. for 24 h. The results are shown in the following Table 5.

TABLE 5

Vertices of the gelling behavior of the PVC top coat
plastisols produced according to example 4, determined
from the gelling curves (viscosity curves)

| Plastisol recipe (according to Ex. 4) | 1** | 2** | 3** | 4* |
|---|---|---|---|---|
| Attainment of a plastisol viscosity of 1000 Pa * s at [° C.] | 89 | 123 | 101 | 122 |
| Attainment of a plastisol viscosity of 10 000 Pa * s at [° C.] | 103 | 139 | 126 | 140 |
| Maximum plastisol viscosity [Pa * s] | 29 300 | 13 500 | 20 600 | 13 700 |
| Temperature on reaching the maximum plastisol viscosity [° C.] | 137 | 146 | 137 | 145 |

**= comparative example
*= according to the invention

The gelling of the plastisol according to the invention proceeds far more slowly than that of the DINP standard plastisol, but almost coincides with the di(isononyl)adipate-based plastisol. The plastisol based on di(2-ethylhexyl)succinate occupies an intermediate position. The slower gelling means, moreover, that even at higher temperatures, reversible forming of the plastisols is still possible without hardening. The deficit in gelling rate relative to the DINP standard plastisols can, if required, be compensated by a person skilled in the art simply by adding other plasticizers, especially quick-gelling plasticizers (e.g. terephthalates with $C_4$ or $C_5$ ester chains or benzoates with $C_5$ to $C_{13}$ ester groups).

EXAMPLE 7

Determination of the Plasticizing Action or the Plasticizer Efficiency on Castings by Determining the Shore Hardness (Shore A)

The Shore hardness is a measure of the softness of a test specimen. The farther the penetration of a standardized needle into the test specimen in a specified measurement time, the lower the measured value. With equal amount of plasticizer, the plasticizer with the highest efficiency produces the lowest value for the Shore hardness. Because in practice formulations/recipes are often adjusted or optimized for a specified Shore hardness, with very efficient plasticizers a certain proportion can accordingly be saved in the recipe, which means a cost reduction for the processor.

For determining the Shore hardness, the plastisols produced according to example 4 were cast in round molds made of brass with a diameter of 42 mm (initial weight: 20.0 g). Then the plastisols in the molds were gelled in an air-circulating drying cabinet for 30 min at 200° C., removed after cooling and stored for at least 24 hours in the drying cabinet (25° C.) prior to measurement. The thickness of the disks was approx. 12 mm. The results of hardness determination are presented in Table 6.

TABLE 6

Shore A hardness determined on castings produced (according
to example 7) from the top coat plastisols containing the diisononyl
succinates according to the invention (according to example 4).

| Plastisol recipe according to Ex. 4 | 1** | 2** | 3** | 4* |
|---|---|---|---|---|
| Shore A | 80 | 79 | 75 | 80 |

**= comparative examples
*= according to the invention

The di(isononyl)succinates according to the invention have the same plasticizer efficiency (relative to the weight of plasticizer) as the known DINP (=standard plasticizer). Therefore esters according to the invention are made available, which have plasticizing action comparable to the DINP-standard at much lower intrinsic viscosity, but are phthalate-free and can be produced on the basis of renewable raw materials.

EXAMPLE 8

Determination of Opacity, Yellowness Index and Exudation Behavior of Top Coat Films The top coat films were produced as described in example 3.1, but using the plastisols from example 4.

Transparency is an essential criterion for quality assessment of PVC top coats for flooring applications, as an optimal overall appearance can only be achieved at high transparency (=low opacity). The transparency of a PVC top coat film is also a measure for the compatibility of the recipe ingredients used for film production, especially as a measure for assessing the compatibility of PVC matrix and plasticizer. High transparency (=low opacity) as a rule means good compatibility. The opacity was determined as described under Analysis, Point 14, using the top coat films produced in example 8.

The yellowness index is another important quality criterion. A yellow coloration in the top coat can lead to considerable impairment of the visual appearance of a decorative floor covering, so that as a rule only very low yellowness indices can be tolerated in the PVC top coat. Yellowing can be caused on the one hand by recipe ingredients (as well as by their by-products and degradation products), and on the other hand it may occur through (e.g. thermal oxidative) degradation during the production process and/or during use of the top coat or floor covering. The yellowness index was determined as described under Analysis, Point 12, using the top coat films produced in example 8.

Assessment of the exudation behavior of the top coat films allows conclusions to be drawn about the permanence of the plasticizers used and other ingredients of the formulation in the fully gelled system. A high level of migration of ingredients of the formulation (which can be reflected for example in the formation of oil films and/or droplets on the film surface) has many practical disadvantages in addition to visual and aesthetic drawbacks. Thus, owing to the increased stickiness there is adherence of dust and/or dirt, which cannot, or at least not completely, be removed again, and therefore leads to a negative appearance in a very short time. In addition, surface haptics is greatly impaired, and there is also increased risk of slipping. Furthermore, through interactions with fastening adhesives there may be uncontrolled detachment of the floor covering. The exudation behavior is assessed using the scoring system shown in Table 7. As exudation is as a rule a so-called "K.O." criterion, only a slight gradation is sensible in the assessment. The films are stored at 25° C. in the period between the assessments.

TABLE 7

Assessment system for assessment of the exudation behavior of top coat films

| Assessment | Meaning |
| --- | --- |
| 1 | Very good (no diffusion or migration discernible; no film formation on the surface). |
| 3 | Good - Satisfactory (no obvious diffusion or migration discernible; minimal film formation on the surface). |
| 5 | Poor (definite migration phenomena; "greasy" haptics; droplet formation; turbidity through segregation). |

The results of assessment of the surface and back are presented in Table 8.

TABLE 8

Results of assessment of the surface and back of the fully gelled top coat films from example 8

| Plastisol recipe (according to Ex. 4) | 1** | 2** | 3** | 4* |
| --- | --- | --- | --- | --- |
| Opacity [—] | 9.7 | 8.8 | 8.9 | 9 |
| Yellowness index [—] | 8.4 | 7.4 | 7.3 | 7.7 |

TABLE 8-continued

Results of assessment of the surface and back of the fully gelled top coat films from example 8

| Plastisol recipe (according to Ex. 4) | 1** | 2** | 3** | 4* |
| --- | --- | --- | --- | --- |
| Assessment of exudation behavior after 24 h | 1 | 1 | 1 | 1 |
| Assessment of exudation behavior after 4 weeks | 1 | 3 | 3 | 3 |

**= comparative example
*= according to the inventon

With respect to opacity and yellowness index, the film produced on the basis of the plastisol according to the invention has a clear advantage over the DINP-standard (1).

In contrast, the compatibility (exudation behavior) is somewhat poorer than for the DINP. The slight deficit in compatibility relative to the DINP standard plastisols can if required easily be compensated again by a person skilled in the art either by adding other plasticizers, especially quick-gelling plasticizers (e.g. terephthalates with $C_4$ or $C_5$ ester chains or benzoates with $C_5$ to $C_{13}$ ester groups) or else by adjusting the processing conditions (e.g. higher gelling temperature).

EXAMPLE 9

Determination of the Thermal Stability of the Top Coat Films

The thermal stability was investigated using a frame design specially developed for this task on/in a Mathis Thermotester (type LTE-TS; from Mathis AG). The testing frame is first moved fully into the oven zone, and then is withdrawn from the oven at a specified rate of travel, so that regions with different residence times (=different temperature loading) are produced on the sample strips. The film produced in example 8 was used as the basis for preparing the test strips. The specimens were first trimmed with guillotine shears. The lateral edges of the film were removed first, so that the film had a width of 20 cm. Then in each case two strips (20*2 cm) were cut off. The strips were placed in succession in a rail of the aforementioned frame for determining the thermal stability, and were secured with a metal clamp and adhesive tape, giving a total length of approx. 40 cm. The 4 outermost rails in the frame were left unoccupied (exclusion of inhomogeneous temperature distribution in the edge zone of the furnace). The following parameters were set on the Mathis Thermotester (type LTE-TS from Mathis AG):
Temperature: 200° C.
Travel range of the testing frame: 28 mm
Time interval: 1 min
Rotary speed of fan: 1800 rev/min After establishment of the temperature, the frame was locked into the guide of the Thermotester and the measurement was started.

Using a Byk colorimeter (Spectro Guide 45/0 from Byk Gardner), L*a*b* incl. a yellowness index Y were determined according to Index D1925. The type of light employed C/2° and the use of a specimen observer were used to achieve optimal measurement results. The thermal stability strips were now measured at each feed (28 mm). The measured values were determined behind a white tile. The yellow coloration already present immediately after production of the films (see Table 8) was used as "zero value", i.e. was deducted from the values found.

TABLE 9

Yellowness indices of the top coat films produced in example 8 after different times of thermal loading at 200° C.

| Plastisol recipe (according to Ex. 4) | 1** | 2** | 3** | 4* |
|---|---|---|---|---|
| Yellowness index [—] after 2 min @ 200° C. | 0 | 0 | 0 | 0 |
| Yellowness index [—] after 4 min @ 200° C. | 2.7 | 1.2 | 0.1 | 0.6 |
| Yellowness index [—] after 6 min @ 200° C. | 17.1 | 29 | 5.8 | 7.4 |
| Yellowness index [—] after 8 min @ 200° C. | 59.4 | 86 | 26 | 28 |

**= comparative example
*= according to the invention

The film that was produced on the basis of the plastisol according to the invention has, surprisingly, a much improved thermal stability compared to the DINP standard sample (1), but also compared to the di(isononyl)adipate sample (2). Therefore transparent PVC films are made available, which have a far higher tolerance to temperature fluctuations and a longer oven residence time, than is known from the prior art.

EXAMPLE 10

Use of Diisononyl Ester of Succinic Acid (Diisononyl Succinate) in PVC Top Coat Formulation (Plastisol) Together with Other Plasticizers—Production of the Top Coat Plastisols As discussed in examples 4 to 9, certain material parameters of the formulations, recipes or semifinished products producible therefrom according to the invention can in principle be adjusted by combining the succinate esters according to the invention with further plasticizers. The following examples explain the advantages of these plasticizer combinations in more detail. The plastisols were prepared according to example 3.1 but with an amended recipe. The weights of the components used for the various plastisols are shown in the following Table 10.

TABLE 10

PVC top coat recipes with plasticizer combinations
[all information in phr (=parts by weight per 100 parts by weight PVC)]

| Plastisol recipe | 1** | 2* | 3* | 4* | 5* | 6* | 7* | 8* |
|---|---|---|---|---|---|---|---|---|
| Vestolit B 7021 --Ultra | 100 | 100 | 100 | 100 | 100 | 100 | 100 | 100 |
| VESTINOL@ 9 | 50 | | | | | | | |
| Di(nonyl)succinate according to Ex. 2.3 | | 50 | 45 | 40 | 30 | 20 | 20 | 20 |
| Unimoll AGF | | | | | 10 | 20 | | |
| Grindstedt's Soft'n Safe | | | | | | | 20 | |
| Isosorbide diisononyl ester | | | | | | | | 20 |
| Drapex 39 | 3 | 3 | 3 | 3 | 3 | 3 | 3 | 3 |
| Mark CZ 149 | 2 | 2 | 2 | 2 | 2 | 2 | 2 | 2 |

**= comparative example
*= according to the invention

The materials and substances used that are not already given in the preceding examples are explained in more detail below:

Unimoll AGF: Glycerol acetate mixture; plasticizer; Lanxess AG.

Grindstedt's Soft'n Safe: Octadecanoic acid-12-(acetyloxy)-2,3-bis(acetyloxy)propyl ester; glycerol triester produced on the basis of castor oil; plasticizer; from Danisco A/S.

Isosorbide diisononyl ester: Laboratory product prepared according to DE 102007006442A1, example 2.

EXAMPLE 11

Determination of the Plastisol Viscosity of Top Coat Plastisols Containing Dinonyl Succinates and Further Plasticizers after a Storage Time of 24 h (at 25° C.)

The viscosities of the plastisols produced in example 10 were measured with a Physica MCR 101 rheometer (from Paar-Physica), according to the procedure described under Analysis, Point 11. The results are shown in the following Table 11 for example for shear rates of 100/s, 10/s, 1/s and 0.1/s.

TABLE 11

Shear viscosity of the plastisols from example 10 after 24 h storage at 25° C.

| Plastisol recipe according to Ex. 10 | 1** | 2* | 3* | 4* | 5* | 6* | 7* | 8* |
|---|---|---|---|---|---|---|---|---|
| Shear viscosity at shear rate = 100/s [Pa * s] | 6.2 | 0.95 | 1.5 | 2.7 | 3.5 | 5.5 | 12.2 | 12.7 |
| Shear viscosity at shear rate = 10/s [Pa * s] | 2.9 | 0.58 | 0.77 | 1.1 | 1.3 | 1.9 | 3.3 | 2.8 |
| Shear viscosity at shear rate = 1/s [Pa * s] | 2.7 | 0.62 | 0.82 | 1.2 | 1.5 | 2.3 | 3.2 | 2.3 |
| Shear viscosity at shear rate = 0.1/s [Pa * s] | 3.3 | 0.87 | 1.2 | 1.8 | 2.5 | 4.4 | 5.1 | 3.3 |

**= comparative example
*= according to the invention

In regard to their plastisol viscosity, the plastisols according to the invention that only contain the diisononyl succinates according to the invention ((2) to (4)) are all well below the values reached by the DINP standard plastisol (1), even with a significantly (by approx. 20%) reduced amount of plasticizer. This means in particular that in many industrially important application techniques (e.g. knife application) these plastisols according to the invention can be applied more quickly. Also in a combination of diisononyl succinate according to the invention and other plasticizers ((5) to (8)), to a large part (furthermore with total amount of plasticizer reduced by 20%) much lower plastisol viscosities are obtained than with the DINP standard plastisol. Only the mixture of diisononyl succinate according to the invention and the glycerol ester Grindsted's Soft'n Safe (7) shows a (slightly) increased plastisol viscosity relative to the DINP standard plastisol. Therefore plastisols according to the invention are made available that have significantly improved processability relative to the known DINP standard, and in particular permit a much higher processing speed in many relevant application techniques.

EXAMPLE 12

Determination of the Gelling Behavior of the PVC Top Coat Plastisols Produced in Example 10

The gelling behavior of the PVC top coat plastisols produced in example 10 was investigated as described under Analysis, Point 12 (see above), with a Physica MCR 101 in oscillation mode after storing the plastisols at 25° C. for 24 h. The results are shown in the following Table 12.

TABLE 12

Vertices of the gelling behavior of the PVC top coat plastisols produced according to example 10, determined from the gelling curves (viscosity curves)

| Plastisol recipe (according to Ex. 10) | 1** | 2* | 3* | 4* | 5* | 6* | 7* | 8* |
|---|---|---|---|---|---|---|---|---|
| Attainment of a plastisol viscosity of 1000 Pa * s at [° C.] | 87 | 120 | 111 | 94 | 85 | 82 | 83 | 86 |
| Attainment of a plastisol viscosity of 10 000 Pa * s at [° C.] | 99 | 136 | 133 | 127 | 124 | 94 | 90 | 109 |
| Maximum plastisol viscosity [Pa * s] | 26700 | 14700 | 16300 | 15900 | 17300 | 29700 | 27900 | 27100 |
| Temperature on reaching the maximum plastisol viscosity [° C.] | 139 | 144 | 139 | 135 | 144 | 139 | 142 | 144 |

**= comparative example
*= according to the invention

The diisononyl succinates according to the invention alone only bring about gelling similar to DINP at much lower plasticizer concentration in the plastisol (−20% compared to the DINP standard plastisol (1)). Although a similar initial rate is reached (4), the further progress of gelling, and especially the maximum plastisol viscosity attainable in the fully gelled state, remains well behind that of the DINP standard plastisol. However, combining isononyl succinates according to the invention with other plasticizers can immediately compensate this difference and in some cases ((6) and (7)) even leads to faster gelling and attainment of higher maximum viscosities in the fully gelled state. In particular, the combination of succinate plasticizers according to the invention and further plasticizers that are based on glycerol esters therefore appears to be particularly advantageous, especially as in comparison with the DINP standard plastisol, a considerable decrease of the total plasticizer concentration in the plastisol (and therefore a much higher economic effectiveness) can be achieved, at the same time without any orthophthalates being present, and an extraordinarily high proportion of the plasticizers can be produced on the basis of renewable raw materials.

EXAMPLE 13

Determination of Water Absorption and Washout Behavior on Top Coat Test Specimens Water absorption and washout behavior are two important criteria in the assessment of the quality of PVC floor coverings. If PVC flooring absorbs water to a large extent, this leads to changes on the one hand in its material properties, and on the other hand also in its visual appearance (e.g. fogging). Therefore high water absorption is as a rule undesirable. The washout behavior is an additional criterion for the permanence of the ingredients of the formulation in the conditions of use (e.g. for floor coverings or roofing sheets). This applies in particular to stabilizers, plasticizers and/or their constituents, as a decrease in concentration in PVC flooring with these recipe ingredients can both impair the material properties and dramatically reduce the service life of the floor covering. Therefore water absorption and washout behavior are of particular importance especially in the upper layers of flooring—such as in the transparent top coat for example.

Fully gelled 1-mm polymer films (gelling conditions in the Mathis oven: 200° C./2 min) were used for determining water resistance. Circles with a diameter of 3 cm were cut out of the films as test specimens. Before storage in water, the circles were stored for 24 hours at 25° C. in a desiccator equipped with a drying agent (KC drying beads). The starting weight (initial weight) was determined with an analytical balance to an accuracy of 0.1 mg. The circles were now stored under the surface of the water in a shaking bath with suitable specimen holders (type: WNB (40 l); manufacturer: the company Memmert) filled with deionized water at a temperature of 30° C. for 24 hours and with continuous movement. After storage, the circles were removed from the water bath, dried and weighed (weight after 24 h). The weighed circles were put in the water bath again and weighed again in the dried state after 7 days (weight after 7 days). After the second weighing, the circles were once again stored at 25° C. for 24 hours in a desiccator equipped with a drying agent (KC drying beads) and then weighed again (final weight=weight after drying). The weight changes were calculated as a percentage and are shown in Table 13.

TABLE 13

Water absorption and washout behavior determined
on top coat test specimens produced according to example 13.

| Plastisol recipe according to Ex. 10 | 1** | 2* | 3* | 4* | 5* | 6* | 7* | 8* |
|---|---|---|---|---|---|---|---|---|
| Weight change after 1 day [wt %] | +0.9 | +1.2 | +1.1 | +1.1 | +0.9 | +0.8 | +1.1 | +0.9 |
| Weight change after 7 days [wt %] | +1.2 | +1.6 | +1.5 | +1.5 | +1.3 | +1.1 | +1.4 | +1.2 |
| Weight change after drying [wt %] | +0.2 | +0.2 | +0.1 | +0.2 | −0.1 | −0.3 | +0.1 | ±0 |

**= comparative example
*= according to the invention

The test specimens that contain the diisononyl succinates according to the invention essentially have water absorption or washout behavior similar to the DINP-standard, with only slight effects occurring in both cases. The combination of diisononyl succinates according to the invention and isosorbide ester has a particularly low water absorption, and at the same time shows neither binding of water to the substrate nor washout, which can be assessed as particularly advantageous.

EXAMPLE 14

Determination of Plasticizing Action or of Plasticizer Efficiency on Castings by Determining the Shore Hardness (Shore A)

The castings were produced according to the procedure described in example 7, but using the plastisols produced according to example 10. The Shore hardness was determined according to the procedure described under Analysis, Point 14 (see above). The results of the hardness determination are presented in the following Table 14.

TABLE 14

Shore A hardness determined on castings produced from
diisononyl succinates and top coat plastisols containing
further plasticizers (according to example 10)

| Plastisol recipe according to Ex. 10 | 1** | 2* | 3* | 4* | 5* | 6* | 7* | 8* |
|---|---|---|---|---|---|---|---|---|
| Shore A | 81 | 79 | 83 | 87 | 86 | 85 | 86 | 89 |

**= comparative example
*= according to the invention

When used alone ((2) to (4)), the diisononyl succinates according to the invention have a plasticizing action similar to that of DINP, even with a plasticizer reduction by 10% (3). On reducing the total amount of plasticizer by 20%, there is a slight decrease in plasticizing action, and even using plasticizer combinations with glycerol esters and isosorbide esters it cannot be raised readily to the DINP level. As one possibility for solving this problem, a person skilled in the art can use quick-gelling plasticizers (so-called quick-gelling agents), e.g. benzoates, citric acid esters, alkylsulfonates etc.

EXAMPLE 15

Determination of Opacity, Yellowness Index and Exudation Behavior of the Top Coat Films The top coat films were produced as described in example 3.1, but using the plastisols produced according to example 10.

The opacity was determined according to the procedure described under Analysis, Point 15 (see above).

The yellowness indices of the top coat films were determined according to the procedure described under Analysis, Point 13 (see above).

Assessment of the exudation behavior was carried out according to the procedure described in example 8 using the scoring system shown in Table 7.

The results of assessment of the surface and back are presented in Table 15.

TABLE 15

Results of assessment of surface and back
of the fully gelled top coat films from example 15

| Plastisol recipe (according to Ex. 10) | 1** | 2* | 3* | 4* | 5* | 6* | 7* | 8* |
|---|---|---|---|---|---|---|---|---|
| Opacity [—] | 10.1 | 10 | 10.7 | 12.4 | 12.9 | 13.5 | 11.5 | 13.7 |
| Yellowness index [—] | 8.5 | 8.3 | 9 | 9.7 | 10.1 | 10.3 | 9.2 | 10.3 |
| Assessment of exudation behavior after 24 h (at 25° C.) | 1 | 1 | 1 | 1 | 1 | 1 | 1 | 1 |
| Assessment of exudation behavior after 4 weeks (at 25° C.) | 1 | 3 | 3 | 3 | 5 | 5 | 3 | 3 |

**= comparative example
*= according to the invention

When only the diisononyl succinates according to the invention ((2) to (4)) are used, values similar to the DINP-standard (1) are achieved both with respect to opacity/transparency and with respect to the yellowness index. With combinations of diisononyl succinates according to the invention and further plasticizers, there is a decrease in transparency with simultaneous increase in yellowness index. The samples are, however, still in the acceptable range, especially as the total amount of plasticizer is greatly reduced in comparison with the DINP sample. Regarding exudation behavior, all samples except the combination of diisononyl succinates according to the invention and Unimoll AGF have acceptable performance. The slight disadvantages both in opacity and in exudation behavior can easily be compensated by a person skilled in the art by processing and/or formulation measures, for example by adding small amounts of plasticizers with faster gelling (compared to the diisonoyl succinates used according to the invention).

EXAMPLE 16

Preparation of Filled and Pigmented Expandable/Foamable PVC Plastisols for Use for Special-Effect Foams In the following, the advantages of the plastisols according to the invention will be illustrated with thermally expandable PVC plastisols containing filler and pigment, which are suitable for producing special-effect foams (foams with special surface structure). These foams are also often referred to as "bouclé foams" from the form of appearance known from the textile area. The following plastisols according to the invention are representative inter alia for example for thermally expandable plastisols, which are used in the production of wall coverings. In particular the following plastisols according to the invention are for example for foam layers that find application in PVC wallpapers.

The plastisols were produced as in example 3.5 but with an amended recipe. The initial weights of the ingredients used for the various plastisols are shown in the following Table 16.

TABLE 16

Composition of the filled and pigmented expandable PVC plastisols from example 10 [all information in phr (=parts by weight per 100 parts by weight PVC)]

| Plastisol recipe | 1** | 2* | 3* | 4* | 5* | 6* | 7* | 8* |
|---|---|---|---|---|---|---|---|---|
| Vestolit E 7012 S | 100 | 100 | 100 | 100 | 100 | 100 | 100 | 100 |
| VESTINOL ® 9 | 54 | | | | | | | |
| Di(nonyl)-succinate according to Ex. 2.3 | | 54 | 49 | 44 | 34 | 24 | 24 | 24 |
| Unimoll AGF | | | | | 10 | 20 | | |
| Grindstedt's Soft'n Safe | | | | | | | 20 | |
| Isosorbide diisononyl ester | | | | | | | | 20 |
| Unicell D200A | 5 | 5 | 5 | 5 | 5 | 5 | 5 | 5 |
| Calibrite-OG | 30 | 30 | 30 | 30 | 30 | 30 | 30 | 30 |
| Kronos 2220 | 8 | 8 | 8 | 8 | 8 | 8 | 8 | 8 |
| Baerostab KK 48-1 | 3 | 3 | 3 | 3 | 3 | 3 | 3 | 3 |
| Isopar J | 3 | 3 | 3 | 3 | 3 | 3 | 3 | 3 |
| Isopropanol | 3 | 3 | 3 | 3 | 3 | 3 | 3 | 3 |

**= comparative example
*= according to the invention

The materials and substances used, if not already given in the previous examples, are explained in more detail below:

Vestolit E 7012 S: Emulsion PVC (homopolymer) with a K value (determined according to DIN EN ISO 1628-2) of 67; from Vestolit GmbH.

Unicell D200A: Azodicarbonamide; thermally activatable blowing agent; from Tramaco GmbH.

Calibrite-OG: Calcium carbonate; filler; from OMYA AG.

KRONOS 2220: Rutile pigment ($TiO_2$) stabilized with Al and Si; white pigment; from Kronos Worldwide Inc.

Baerostab KK 48-1: Potassium/zinc "kicker"; decomposition catalyst for thermal blowing agent; lowers the substance-specific decomposition temperature of the blowing agent; simultaneously also stabilizing action; from Baerlocher GmbH.

Isopar J: Isoparaffin, cosolvent for lowering plastisol viscosity; from Möller Chemie.

Isopropanol: Cosolvent for lowering plastisol viscosity and additive for improving foam structure (from Brenntag AG).

EXAMPLE 17

Determination of the Plastisol Viscosity of the Filled and Pigmented Thermally Expandable Plastisols from Example 16 after a Storage Time of 24 h (at 25° C.)

The viscosity of the plastisols produced in example 16 was measured as described under Analysis, Point 11 (see above), with a Physica MCR 101 rheometer (from Paar-Physica). The results are shown in the following Table 17 as an example for shear rates of 100/s, 10/s, 1/s and 0.1/s.

TABLE 17

Shear viscosity of the plastisols from example 16 after 24 h storage at 25° C.

| Plastisol recipe according to Ex. 16 | 1** | 2* | 3* | 4* | 5* | 6* | 7* | 8* |
|---|---|---|---|---|---|---|---|---|
| Shear viscosity at shear rate = 100/s [Pa * s] | 4 | 1.1 | 1.4 | 1.9 | 2.1 | 2.5 | 3.8 | 3.3 |
| Shear viscosity at shear rate = 10/s [Pa * s] | 4.9 | 1.5 | 2 | 2.6 | 3 | 3.4 | 4.7 | 3.9 |
| Shear viscosity at shear rate = 1/s [Pa * s] | 9.1 | 3.5 | 4.6 | 6.2 | 7.1 | 8.1 | 10.5 | 8.5 |
| Shear viscosity at shear rate = 0.1/s [Pa * s] | 22.5 | 10.8 | 14.4 | 19.7 | 23 | 26.8 | 32.8 | 25.9 |

**= comparative example
*= according to the invention

All plastisols that contain the diisononyl succinates according to the invention have, starting from a shear rate of $10*s^{-1}$, a much lower shear viscosity than the DINP plastisol (=standard). Both the use of the pure diisononyl succinate and the use of plasticizer combinations are advantageous. In particular it should be noted that even an amount of plasticizer reduced by approx. 20% ((4) compared to (1)) still leads to a much lower plastisol viscosity. It can therefore be assumed that in comparison with DINP, a far smaller amount of plasticizer can be used. Thus, plastisols according to the invention are made available, which in comparison with the current standard (DINP) have a much improved processability, and in particular allow much faster processing speeds, and at the same time a marked reduction in the amount of plasticizer is possible.

EXAMPLE 18

Determination of the Gelling Behavior of the Filled and Pigmented Thermally Expandable Plastisols from Example 16

The gelling behavior of the filled and pigmented thermally expandable plastisols produced in example 16 was investigated as described under Analysis, Point 12 (see above), with a Physica MCR 101 in oscillation mode after storing the plastisols at 25° C. for 24 h. The results are shown in the following Table 18.

TABLE 18

Vertices of the gelling behavior of the filled and pigmented expandable plastisols produced according to example 16, determined from the gelling curves (viscosity curves)

| Plastisol recipe (according to Ex. 16) | 1** | 2* | 3* | 4* | 5* | 6* | 7* | 8* |
|---|---|---|---|---|---|---|---|---|
| Attainment of a plastisol viscosity of 1000 Pa * s at [° C.] | 77 | 106 | 97 | 87 | 82 | 77 | 78 | 81 |
| Attainment of a plastisol viscosity of 10 000 Pa * s at [° C.] | 103 | — | — | — | 130 | 120 | 107 | 112 |
| Maximum plastisol viscosity [Pa * s] | 13800 | 4100 | 6000 | 8500 | 10700 | 10900 | 11600 | 11200 |
| Temperature on reaching the maximum plastisol viscosity [° C.] | 117 | 142 | 140 | 137 | 132 | 124 | 126 | 126 |

**= comparative example
*= according to the invention

At equal plasticizer content (comparison (1) against (2)), the gelling rate of the succinate plasticizers according to the invention is well below the rate of the DINP-standard and the gelling temperature of the succinate plasticizers according to the invention is well above the gelling temperature of the DINP-standard. The plasticizer concentration series ((2) to (4)) clearly shows, however, that the gelling rate or the gelling temperature can clearly be shifted in the direction of the DINP-standard by decreasing the plasticizer content, as is already suggested by the plastisol viscosity (see example 17). The maximum attainable plastisol viscosity in the fully foamed and fully gelled state is also clearly shifted toward the DINP plastisol. By combining with further plasticizers ((5) to (8)), the values reached by the DINP-standard can be reproduced without any difficulty, and a reduction in the total amount of plasticizer by approx. 20% is still possible. Thus, plastisols according to the invention are made available, which display the good gelling properties known from the DINP-standard but with a greatly reduced amount of plasticizer, and at the same time are or can be free from orthophthalates.

EXAMPLE 19

Production and Assessment of the Special-Effect Foam from Filled and Pigmented Thermally Expandable Plastisols from Example 16

The special-effect foam wallpapers were produced according to the procedure described in example 3.5, using the plastisols produced according to example 16, storing the plastisols for 2 h at 25° C. prior to processing.

The yellowness indices were determined on the fully gelled samples as described under Analysis, Point 13 (see above).

For assessing the expansion behavior, the DINP sample is adopted as the comparison standard. Normal expansion behavior (="O.K.") thus corresponds to the behavior of the DINP sample.

For assessing the surface quality or the surface structure, mainly the uniformity or regularity of the surface structures is evaluated. The dimensional extent of the individual components of the special effect is also included in the assessment.

In addition, there is assessment of the backing (paper) with respect to exudation or migration of recipe ingredients. The scoring system on which the assessment of the surface structure is based is reproduced in the following Table 19.

TABLE 19

Assessment system for assessing the surface quality of special-effect foams

| Assessment | Meaning |
|---|---|
| 1 | Very good surface structure (very high regularity and uniformity of the surface effects; size of the individual effects suitable). |
| 2 | Good surface structure (high regularity and uniformity of the surface effects; size of the individual effects suitable). |
| 3 | Satisfactory surface structure (regularity and uniformity of the surface effects acceptable; size of the individual effects reasonable). |
| 4 | Adequate surface structure (slight irregularities or nonuniformities in the surface structure; size of the individual effects easily unbalanced). |
| 5 | Poor surface structure (irregularities and nonuniformities in the surface structure; size of the individual effects unbalanced). |
| 6 | Unsatisfactory surface structure (very irregular and nonuniform surface effects; size of the individual effects unsuitable (much too large/much too small)). |

The scoring system forming the basis of assessment of the wallpaper backing (migration) is reproduced in the following Table 20.

TABLE 20

Assessment system for assessing the backing of special-effect foams

| Assessment | Meaning |
|---|---|
| 1 | Very good (no diffusion or migration discernible; no color variation in the edge zone). |
| 2 | Good (no diffusion or migration discernible; minimal color variation in the edge zone). |
| 3 | Satisfactory (minimum diffusion or migration discernible; definite color variation in the application zone). |
| 4 | Adequate (slight diffusion or migration discernible; definite color variation in the application zone). |
| 5 | Poor (definite migration phenomena; slightly "greasy" haptics; marked color difference in the whole application zone). |
| 6 | Inadequate (high level of migration phenomena; very "greasy" haptics; extreme color difference in the whole application zone). |

The surface structure of a special-effect foam (i.e. a foam that is to have a special/especially pronounced surface structuring) is essentially determined by the constituents and the processing properties of the plastisol used in its manufacture. We may mention in particular the plastisol viscosity, the flow behavior of the plastisol (e.g. characterized by the variation of plastisol viscosity as a function of the shear rate), the gelling behavior of the plastisol (decisive inter alia for the size and distribution of the gas bubbles), the influence of the plasticizer used on the decomposition of the blowing agent (so-called "auto-kick effects"), and the choice and combination of blowing agent(s) and decomposition catalyst(s). These are greatly influenced by the choice of feed materials, especially the plasticizers used, and so can be controlled as desired.

Assessment of the backing of the coated paper allows conclusions to be drawn about the permanence of the plasticizers used and of other ingredients of the formulation in the fully gelled system. A high level of migration of ingredients of the formulation has numerous practical disadvantages, in addition to visual and aesthetic drawbacks. Thus, the increased stickiness leads to adherence of dust, which cannot be removed, or at least not completely, and therefore leads to a negative appearance in a very short time. In addition, migration of ingredients of the formulation as a rule has a very negative effect on printability or on the stability of printing. Furthermore, through interactions with fastening adhesives (e.g. wallpaper adhesive) there may be uncontrolled detachment of a wall covering.

When assessing thermally expandable plastisols, the yellowness index is of interest in two different respects. On the one hand it shows the degree of decomposition of the blowing agent (=yellow in the undecomposed state), and on the other hand it is a measure of the thermal stability (discolorations as a result of thermal loading).

The results of the assessment of the surface and backing are presented in Table 17.

TABLE 21

Results of assessment of the surface and backing of the fully gelled special-effect foams from example 19

| Plastisol recipe (according to Ex. 16) | 1** | 2* | 3* | 4* | 5* | 6* | 7* | 8* |
|---|---|---|---|---|---|---|---|---|
| Expansion behavior | — | O.K. | O.K. | O.K. | O.K. | O.K. | O.K. | O.K. |
| Yellowness index | 9.1 | 9.3 | 10.1 | 10.1 | 10.2 | 10.9 | 9 | 10.8 |
| Assessment of surface quality/ structure | 1 | 4 | 4 | 4 | 3 | 3 | 2 | 3 |
| Assessment of the backing after 24 h | 1 | 1 | 1 | 1 | 1 | 1 | 1 | 1 |
| Assessment of the backing after 168 h | 1 | 2 | 2 | 2 | 2 | 2 | 2 | 2 |

**= comparative example
*= according to the invention

The expansion behavior of all the samples is comparable to that of the DINP standard sample (1). The yellowness indices of the samples were also at a similar level, with a certain range of fluctuation depending on the plasticizer concentration used in the plastisol and the additional plasticizer used. The two plastisols that contain Unimoll AGF have a certain disadvantage, in that Unimoll AGF itself already has a clearly discernible yellowish brown coloration. Regarding surface quality, further potential can be seen regarding recipe optimization, wherein the quality clearly depends in this case on the coplasticizer used. In all cases, no migration of ingredients of the formulation into the wallpaper paper can be seen. Altogether, the combination of isononyl succinate according to the invention and certain glycerol esters (7) proves to be the best, and provides a result comparable to the DINP-standard. Thus, plastisols are made available that make it possible, with clearly increased plasticizer efficiency (i.e. much smaller amount of plasticizer) and greatly improved processability, to produce special-effect foams with quality comparable to the current standard DINP, wherein at the same time a certain proportion of the plasticizers used can (optionally) be based on renewable raw materials and (optionally) an orthophthalate-free composition can be offered.

The invention claimed is:

1. A mixture of succinate esters, comprising at least 60 wt % of C9 diesters, based on 100 weight % of the mixture, wherein
an alkyl residue has a proportion of alkyl components with less than 9 carbon atoms of a maximum of 15 wt %,
an alkyl residue has a proportion of alkyl components with more than 9 carbon atoms of a maximum of 25 wt %,
a proportion of 3,5,5-trimethylhexyl residues is a maximum of 5 mol %, and
a proportion of linear n-nonyl residues is a maximum of 15 mol %.

2. The mixture as claimed in claim 1, wherein a proportion of succinic acid relative to all parts of succinic acid that are present in the mixture as ester, which is based on renewable raw materials, is at least 10 mol %.

3. The mixture of claim 1, wherein a proportion of succinate esters that comprise 3,5,5-trimethylhexyl residue is a maximum of 5 mol %.

4. The mixture of claim 1, wherein the mixture comprises a proportion of alkyl residues with 9 carbon atoms, which have a methyl branching on a second carbon atom after an oxygen of a carboxyl group, of a maximum of 49.5 mol %.

5. The mixture of claim 1, wherein the boiling point is above 180° C.

6. The mixture of claim 1, wherein an intrinsic viscosity determined by shear rheometry with a shear rate of Vs at a temperature of 20° C. is a maximum of 40 mPa·s.

7. A mixture of succinate esters, comprising at least 60 wt % of C9 diesters, based on 100 weight % of the mixture, wherein
an alcohol mixture for preparation has a proportion of alcohol components with less than 9 carbon atoms of a maximum of 15 wt %, and a proportion of alcohol components with more than 9 carbon atoms of a maximum of 25 wt %,
a content of 3,5,5-trimethylhexanol in the alcohol mixture is a maximum of 5 mol %, and
a content of linear n-nonanol in the alcohol mixture is a maximum of 15 mol %.

8. The mixture of claim 7, wherein a proportion of succinic acid or succinic acid derivative for production of the esters, which is based on renewable raw materials, is at least 10 mol %.

9. The mixture of claim 7, wherein a proportion of succinate esters comprising a 3,5,5-trimethylhexyl residue is a maximum of 5 mol %.

10. The mixture of claim 7, wherein the alcohol mixture comprises a proportion of isomeric alcohols with 9 carbon atoms that have a methyl branching on the β-carbon atom of the alcohol of a maximum of 49.5 mol %.

11. The mixture of claim 7, wherein the alcohol mixture comprises a proportion of isomeric alcohols with 9 carbon atoms that have two methyl branchings of a maximum 49.5 mol %.

12. A method of producing the mixture of claim 1, comprising contacting a succinic acid or succinic acid derivative with an isomeric alcohol mixture, with liberation of water or methanol;

wherein up to 50% stoichiometric excess of the alcohol mixture is used; and the reaction takes place in the presence of a catalyst selected from the group consisting of butyl titanate, and nonyl titanate.

13. The method of claim 12, wherein a proportion of succinic acid or succinic acid derivative for production of the esters, which is based on renewable raw materials, is at least 10 mol %.

14. A composition comprising the mixture of claim 1 and a further polymer.

15. The composition of claim 14, wherein the composition additionally comprises at least one plasticizer selected from the group consisting of alkyl benzoate, dialkyladipate, glycerol ester, trialkyl citrate, acylated trialkyl citrate, trialkyl trimellitate, glycol dibenzoate, dialkyl terephthalate, dialkyl phthalate, dialkanoyl ester of isosorbide, and dialkylester of 1,2-, 1,3- or 1,4-cyclohexane dicarboxylic acids.

16. The mixture of claim 1, wherein the mixture is suitable as plasticizer.

17. A molded article comprising the mixture of claim 1.

18. A floor covering comprising the mixture of claim 1.

19. A wall covering comprising the mixture of claim 1.

20. A resist, sealant or adhesive comprising the mixture of claim 1.

21. A film or awning comprising the mixture of claim 1.

* * * * *